(12) United States Patent
Kang et al.

(10) Patent No.: US 11,828,719 B2
(45) Date of Patent: *Nov. 28, 2023

(54) NANO-LIGAND FOR PROMOTING CELL ADHESION AND DIFFERENTIATION OF STEM CELLS AND METHOD OF PROMOTING CELL ADHESION AND DIFFERENTIATION OF STEM CELLS BY USING THE SAME

(71) Applicant: Korea University Research and Business Foundation, Seoul (KR)

(72) Inventors: Hee-Min Kang, Seoul (KR); Chandra Khatua, Seoul (KR); Gun-Hyu Bae, Hwaseong-si (KR); Hyo-Jun Choi, Seoul (KR); Sun-Hong Min, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/186,675

(22) Filed: Feb. 26, 2021

(65) Prior Publication Data

US 2021/0270765 A1 Sep. 2, 2021

(30) Foreign Application Priority Data

Feb. 28, 2020 (KR) .................. 10-2020-0025477
Apr. 24, 2020 (KR) .................. 10-2020-0050356

(51) Int. Cl.
*C12N 5/071* (2010.01)
*C12N 11/14* (2006.01)
(Continued)

(52) U.S. Cl.
CPC ... *G01N 27/3278* (2013.01); *C07K 14/70546* (2013.01); *C12N 5/0075* (2013.01);
(Continued)

(58) Field of Classification Search
CPC ... C07K 4/00; C07K 4/12; C07K 7/06; C07K 17/00; C07K 17/14; C12Q 1/24;
(Continued)

(56) References Cited

U.S. PATENT DOCUMENTS

2017/0285020 A1 10/2017 Mao et al.

OTHER PUBLICATIONS

Translation of KR 10-2020-0050356, filed Apr. 24, 2020. (Year: 2020).*

(Continued)

*Primary Examiner* — Jeffrey E. Russel
(74) *Attorney, Agent, or Firm* — Sughrue Mion, PLLC

(57) ABSTRACT

The present invention relates to a nano-ligand for promoting cell adhesion and differentiation of stem cells and a method of promoting cell adhesion and differentiation of stem cells by using the nano-ligand, and the method of promoting cell adhesion and differentiation of stem cells according to the present invention may temporally and spatially, and reversibly control nano-ligand sliding by applying a magnetic field to a substrate including the nano-ligands, and efficiently control stem cell adhesion and differentiation ex vivo or in vivo through the magnetic-field based on spatiotemporal control.

5 Claims, 19 Drawing Sheets
(12 of 19 Drawing Sheet(s) Filed in Color)
Specification includes a Sequence Listing.

(51) Int. Cl.
  *G01N 27/327* (2006.01)
  *C07K 14/705* (2006.01)
  *C12N 5/00* (2006.01)
(52) U.S. Cl.
  CPC .......... *C12N 11/14* (2013.01); *C12N 2501/40* (2013.01); *C12N 2533/50* (2013.01); *G01N 2203/0635* (2013.01)
(58) Field of Classification Search
  CPC ...... C12N 5/0075; C12N 11/14; C12N 13/00; C12N 2500/30; C12N 2500/50; C12N 2501/40; C12N 2529/00; C12N 2533/00; C12N 2533/30; C12N 2533/50
  See application file for complete search history.

(56) References Cited

OTHER PUBLICATIONS

Cao et al. Evaluating the Effects of Charged Oligopeptide Motifs Coupled with RGD on Osteogenic Differentiation of Mesenchyma Stem Cells. ACS Applied Materials & Interfaces. Mar. 6, 2015, vol. 7, pp. 6698-6705. (Year: 2015).*
Heemin Kang et al., "Immunoregulation of macrophages by dynamic ligand presentation via ligand-cation coordination", Nature Communications, 2019, vol. 10, No. 1696, pp. 1-14 (14 pages total).
Office Action dated Sep. 13, 2022 issued by the Japanese Patent Office in Japanese Application No. 2021-031825.
Office Action dated Mar. 8, 2022 issued by the Japanese Patent Office in Japanese Application No. 2021-031825.
Extended European Search Report dated Jul. 7, 2021 in Application No. 21159272.0.
Dexter S. H. Wong et al., "Magnetically Tuning Tether Mobility of Integrin Ligand Regulates Adhesion, Spreading, and Differentiation of Stem Cells", Nano Letters, Feb. 27, 2017, vol. 17, No. 3, pp. 1685-1695 (11 pages total).
Qui-Yun Chen et al., "Synthesis, characterization, cell imaging and anti-tumor activity of multifunctional nanoparticles", Spectrochimica Acta Part A: Molecular and Biomolecular Spectroscopy, May 3, 2012, vol. 96, pp. 284-288 (5 pages total).
Heemin Kang et al., "Remote Control of Multimodal Nanoscale Ligand Oscillations Regulates Stem Cell Adhesion and Differentiation", ACS Nano, Oct. 24, 2017, vol. 11, No. 10, pp. 9636-9649 (14 pages total).
Chandra Khatua et al., "In Situ Magnetic Control of Macroscale Nanoligand Density Regulates the Adhesion and Differentiation of Stem Cells", Nano Letters, May 14, 2020, vol. 20, No. 6, pp. 4188-4196 (9 pages total).
Jianglin Wang et al., "Phage nanofibers induce vascularized osteogenesis in 3D printed bone scaffolds", Adv. Mater., Aug. 6, 2014, vol. 26, No. 29, pp. 4961-4966 (12 pages).
Dexter S. H. Wong et al., "Magnetically Tuning Tether Mobility of Integrin Ligand Regulates Adhesion, Spreading, and Differentiation of Stem Cells", NANO Letters, 2017, vol. 17, pp. 1685-1695 (11 pages).
Dexter S. H. Wong et al., "Supporting Information: Magnetically Tuning Tether Mobility of Integrin Ligand Regulates Adhesion, Spreading, and Differentiation of Stem Cells", 2017, Department of Mechanical and Automation Engineering (Biomedical Engineering) et al., pp. S-1 to S-19 (19 pages).

* cited by examiner

[FIG. 1]
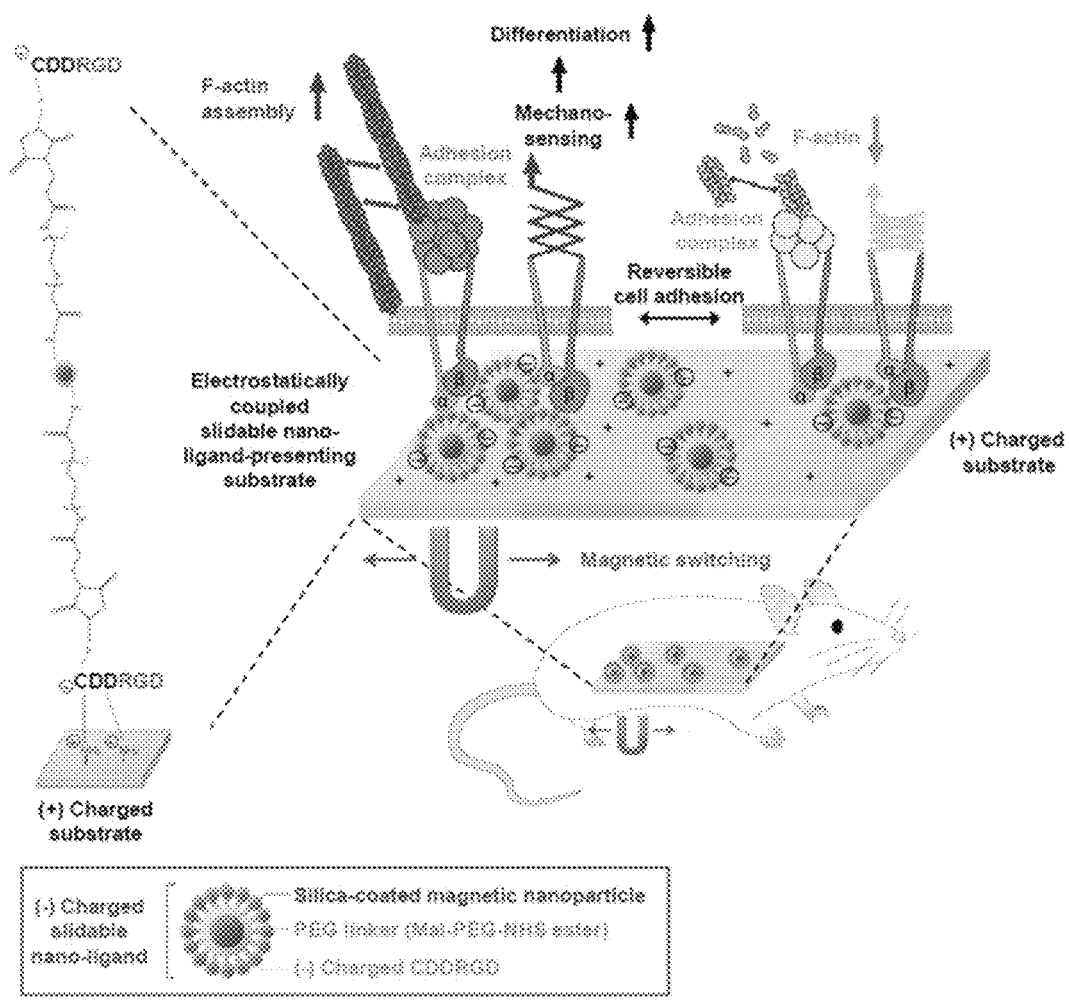

[FIG. 2]
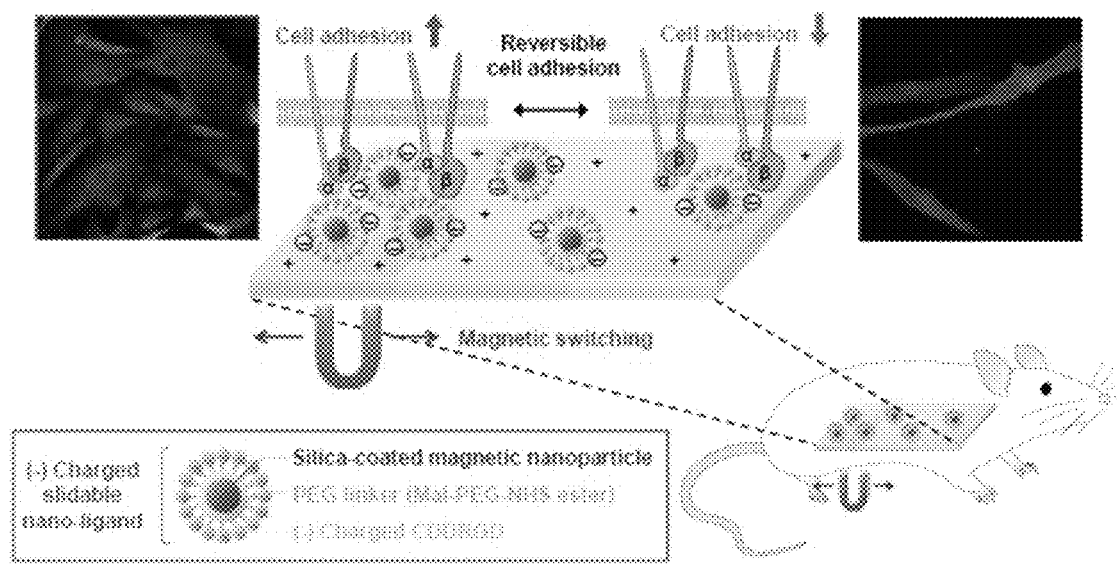
[FIG. 3]
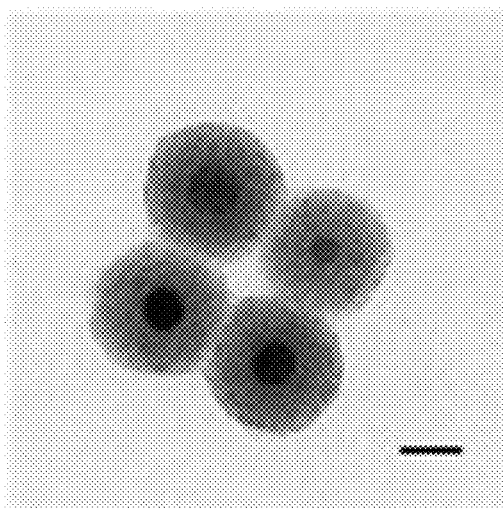

[FIG. 4]
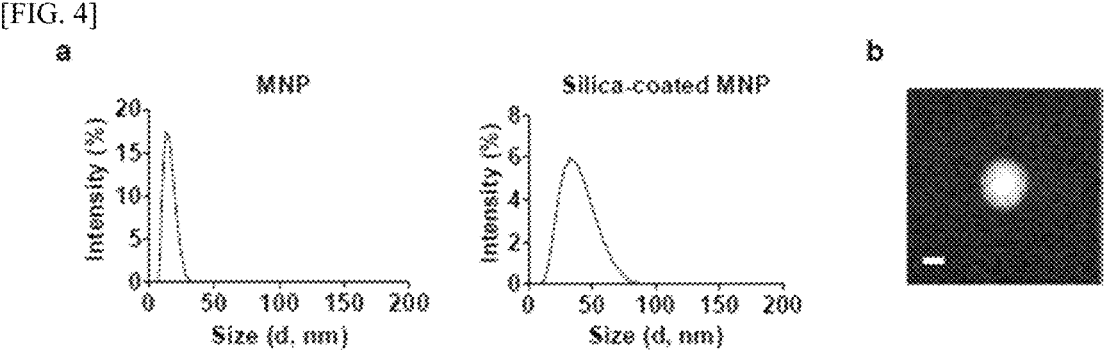
[FIG. 5]
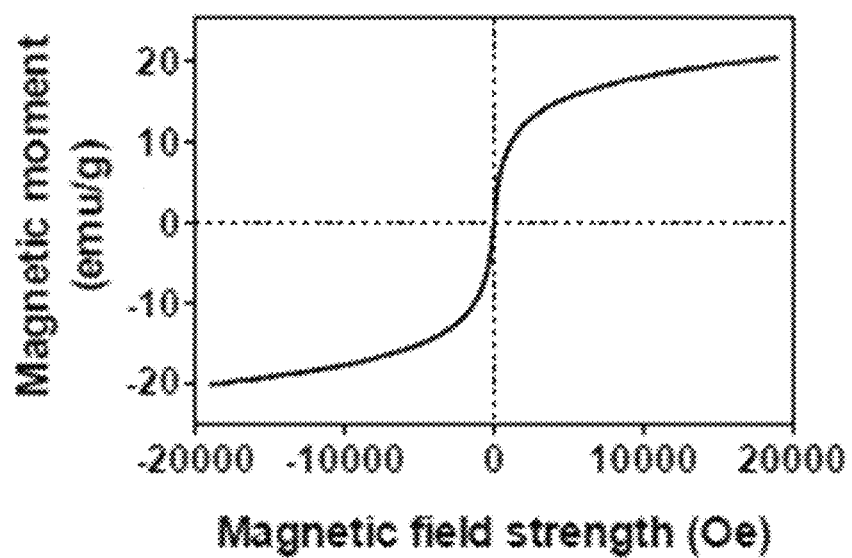

[FIG. 6]
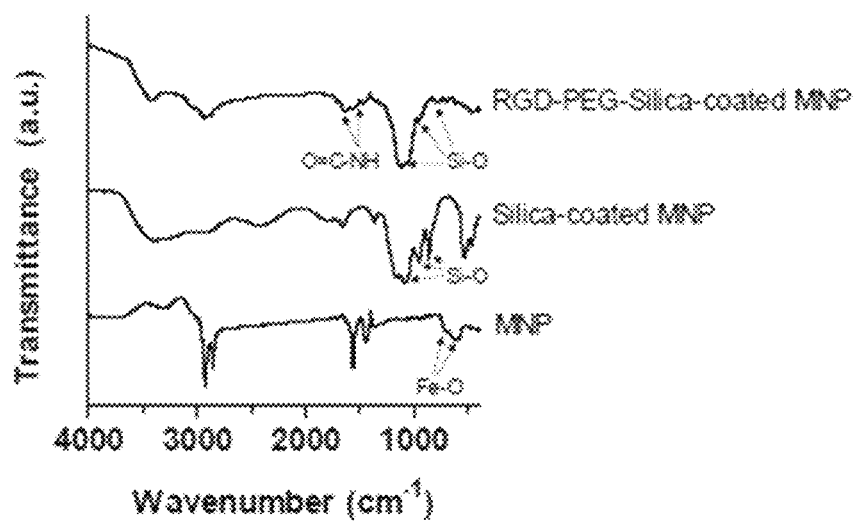

[FIG. 7]
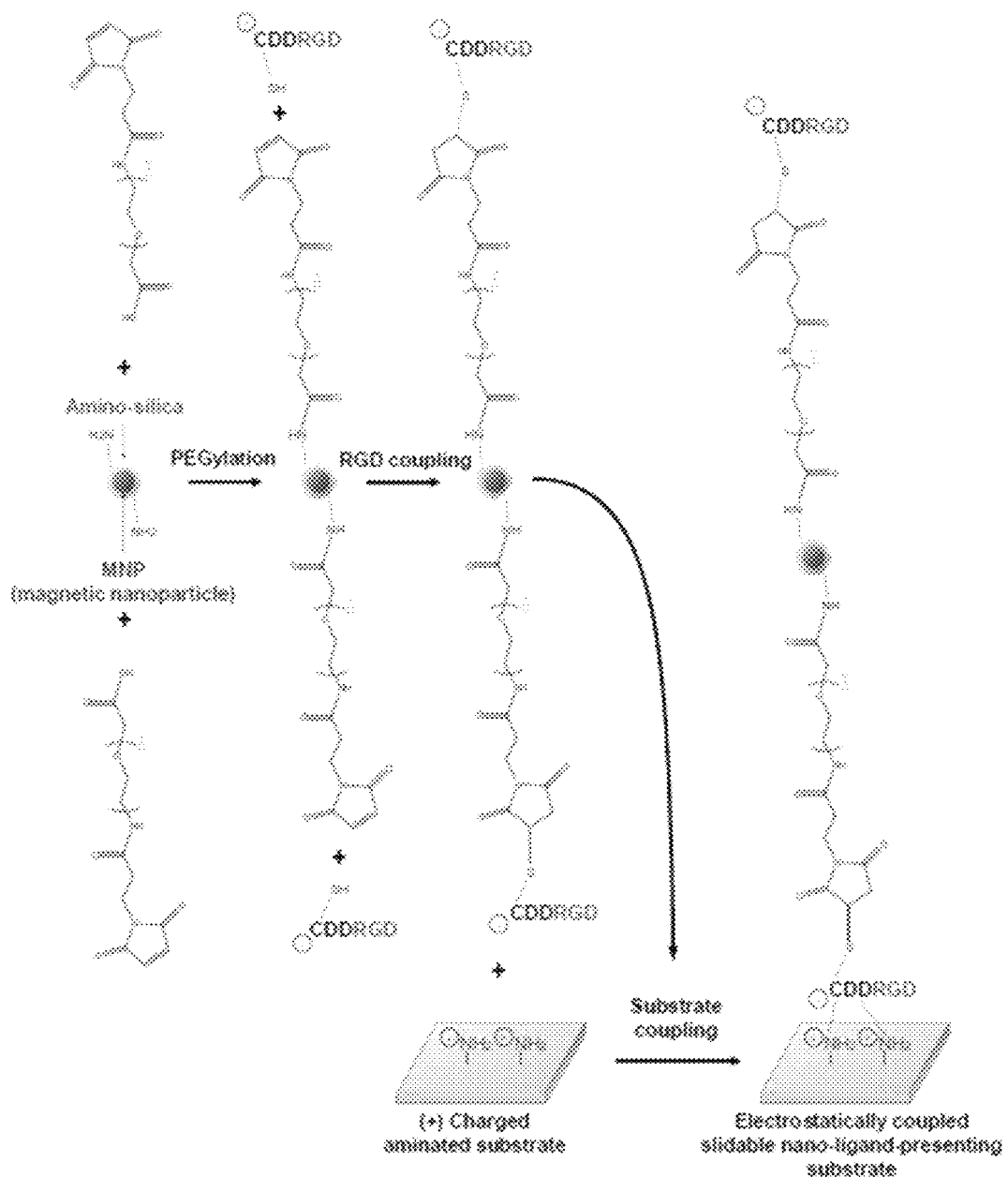

[FIG. 8]
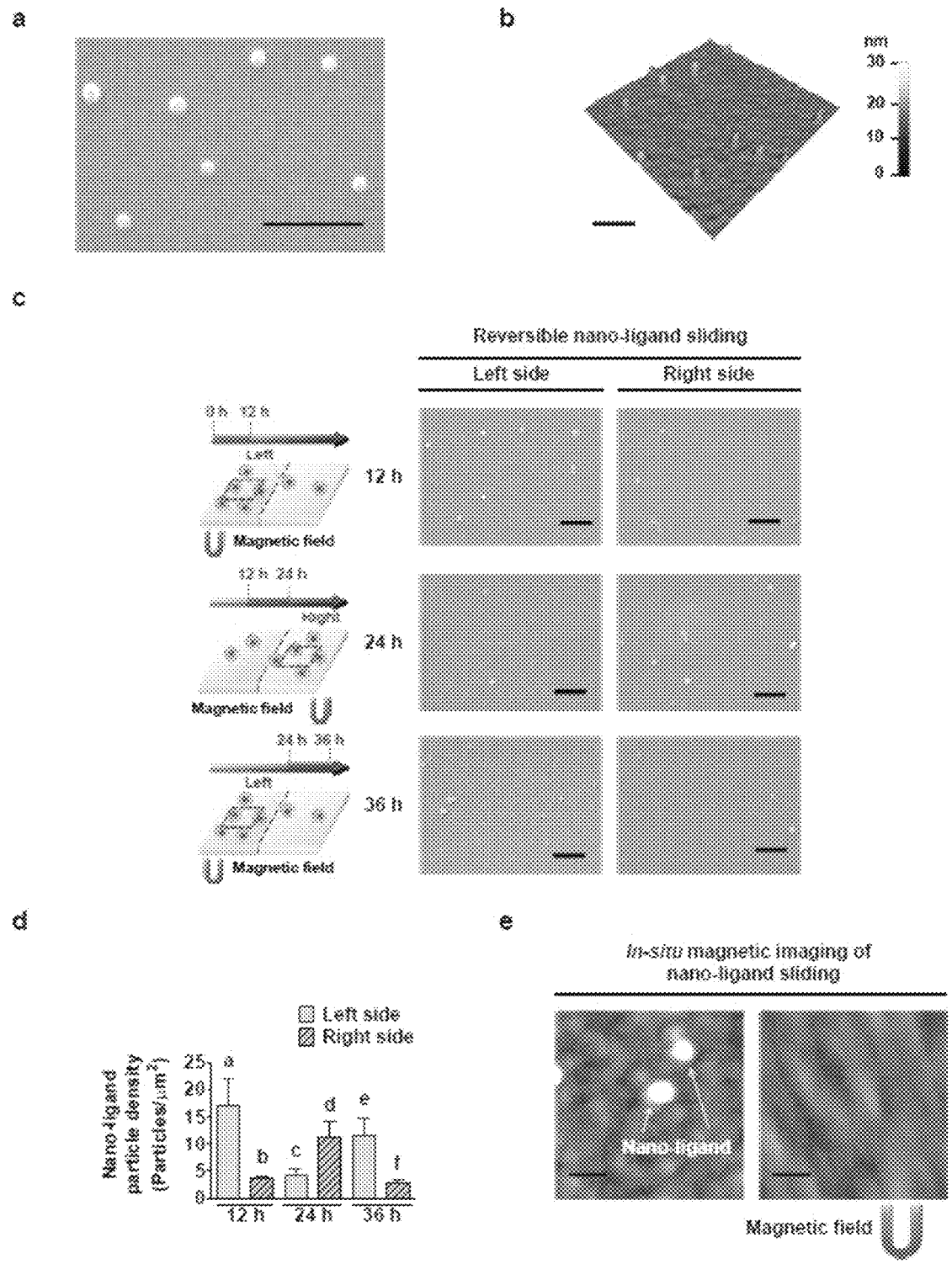

[FIG. 9]
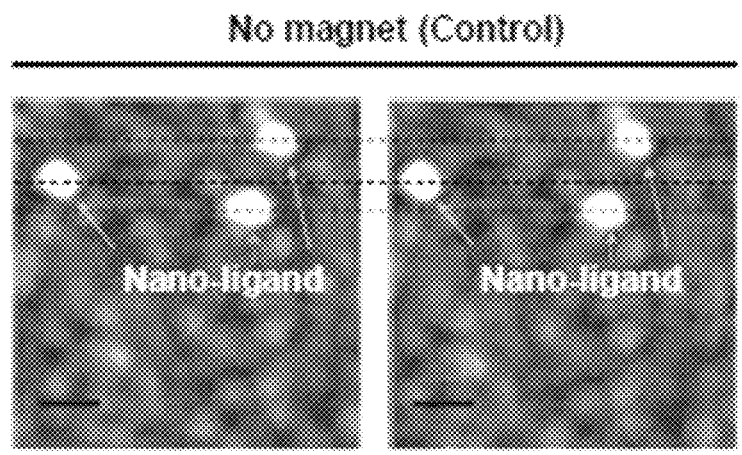
[FIG. 10]
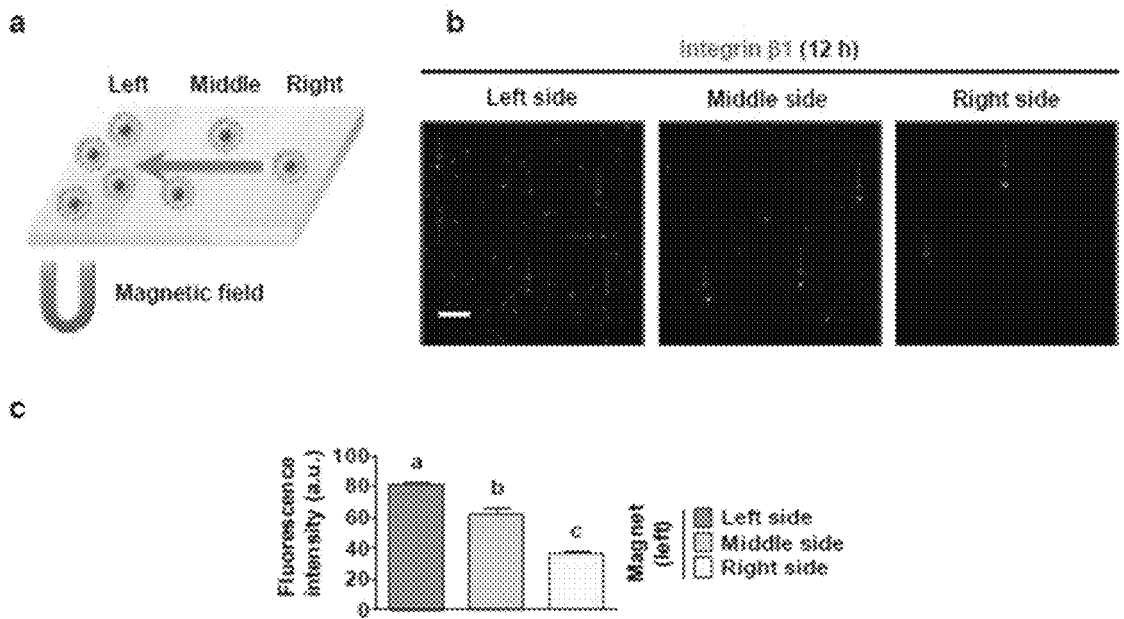

[FIG. 11]
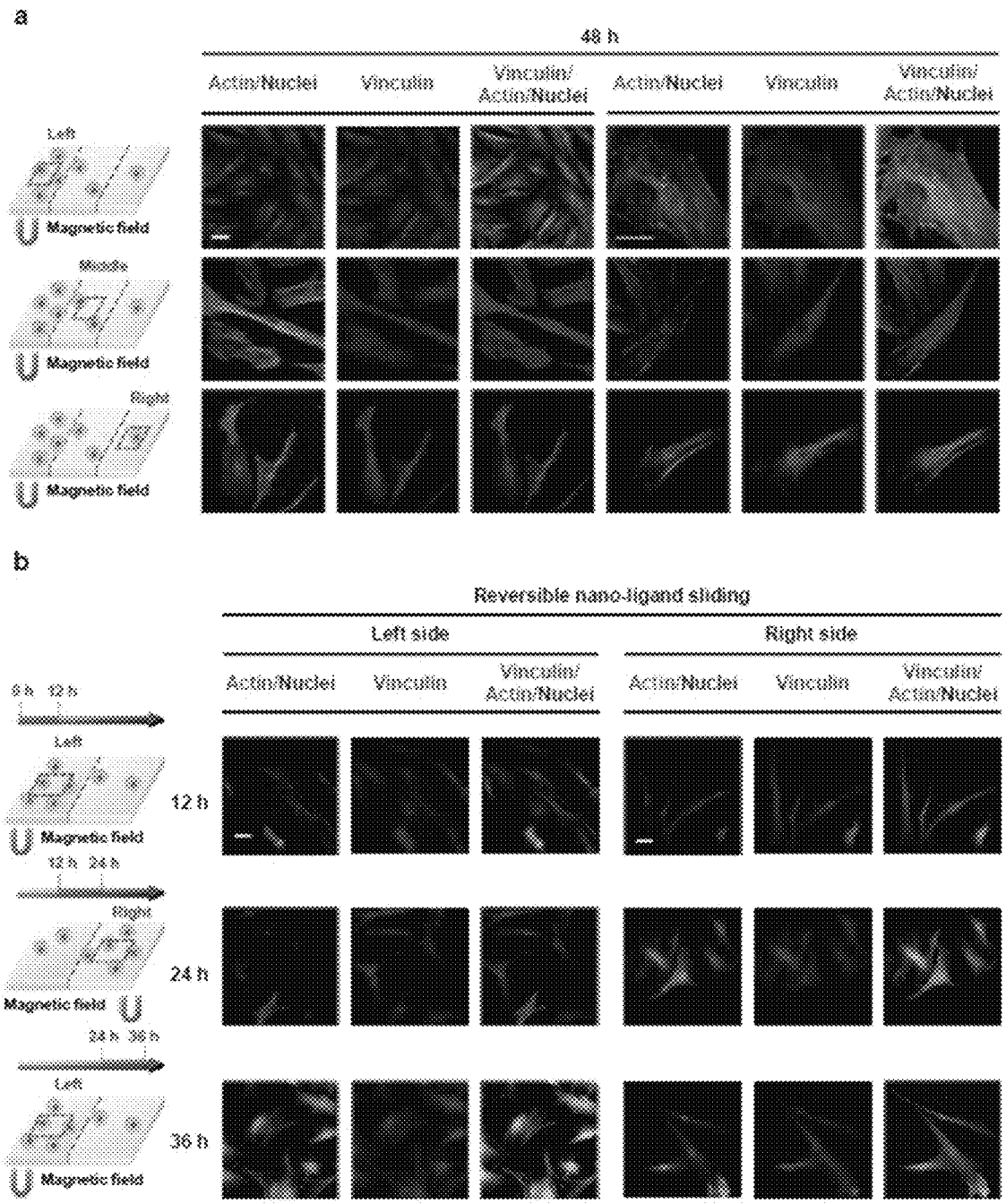

[FIG. 12]
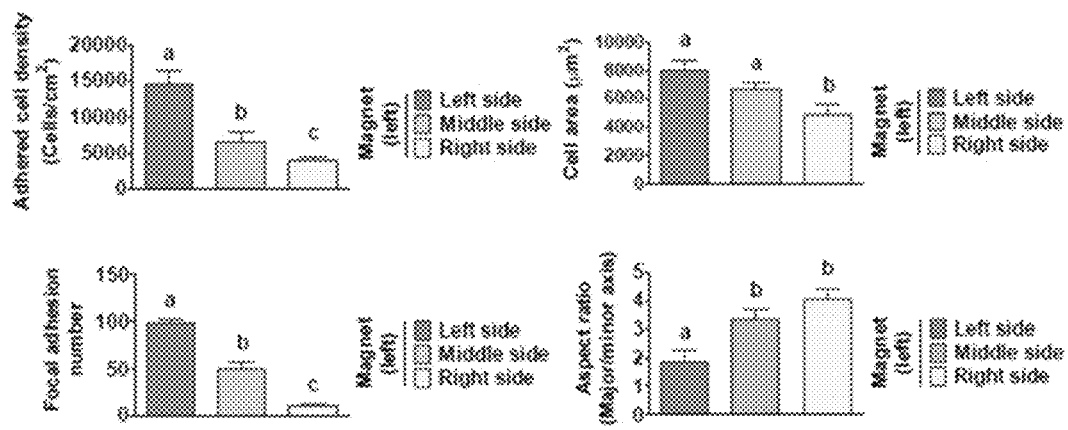

[FIG. 13]
a
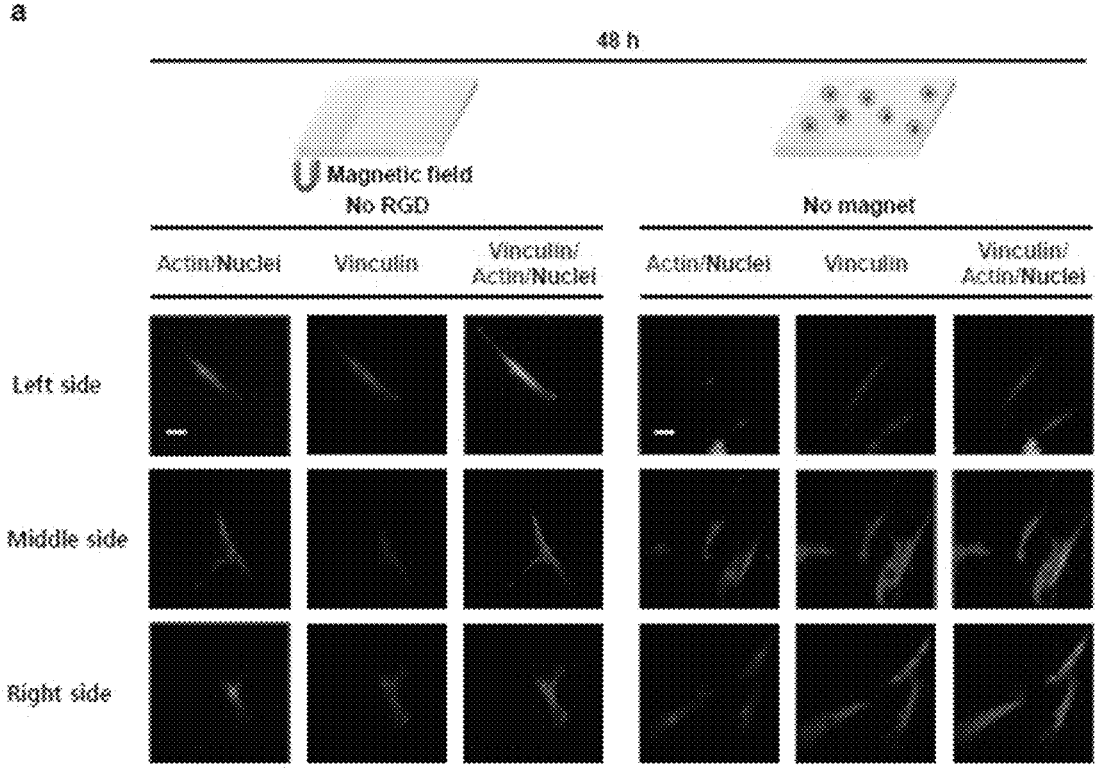
b
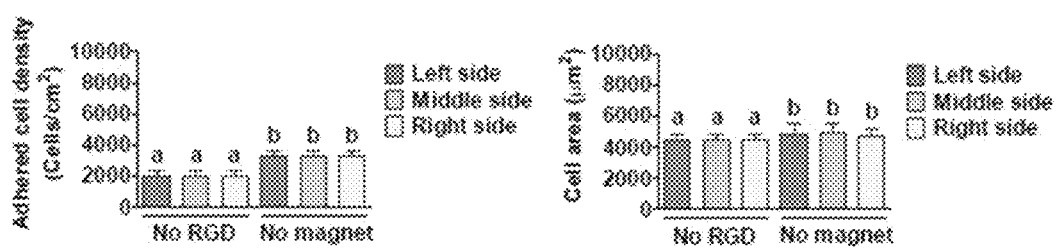

[FIG. 14]
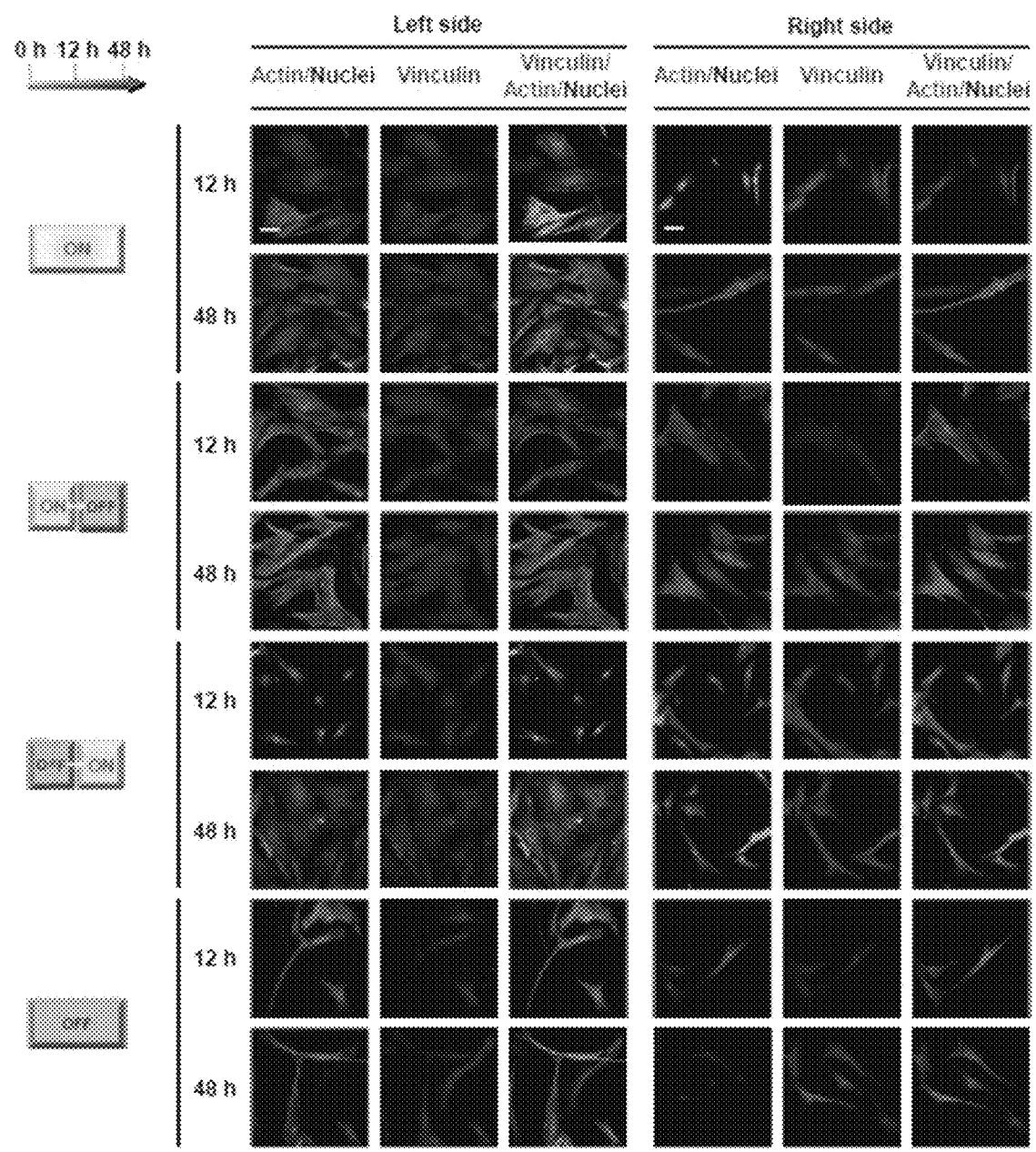

[FIG. 15]
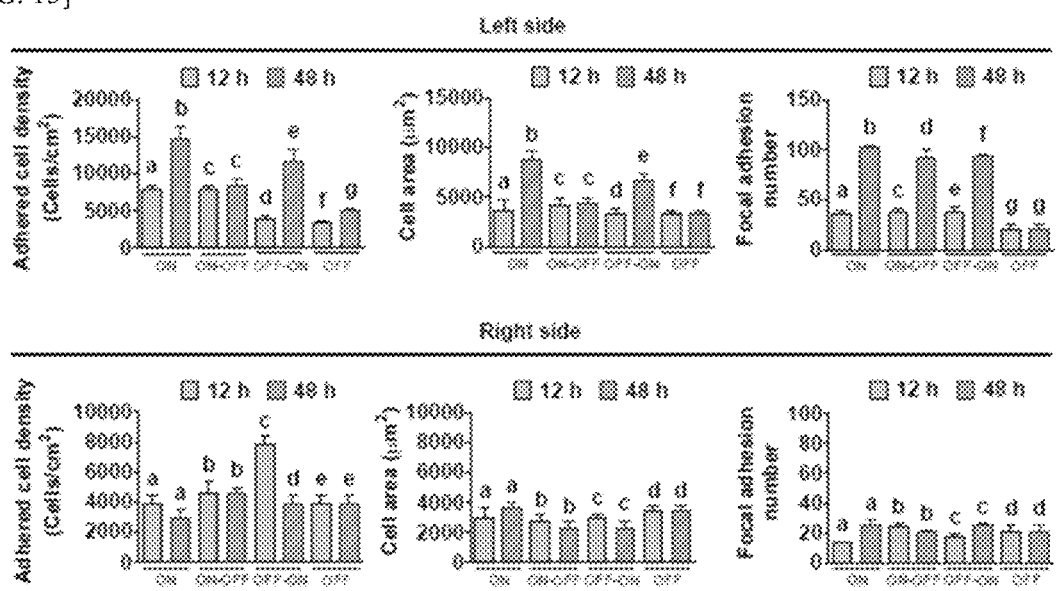
[FIG. 16]
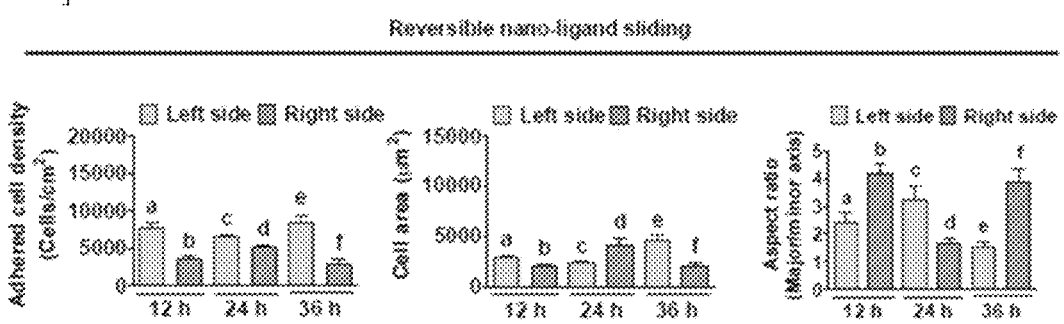

[FIG. 17]
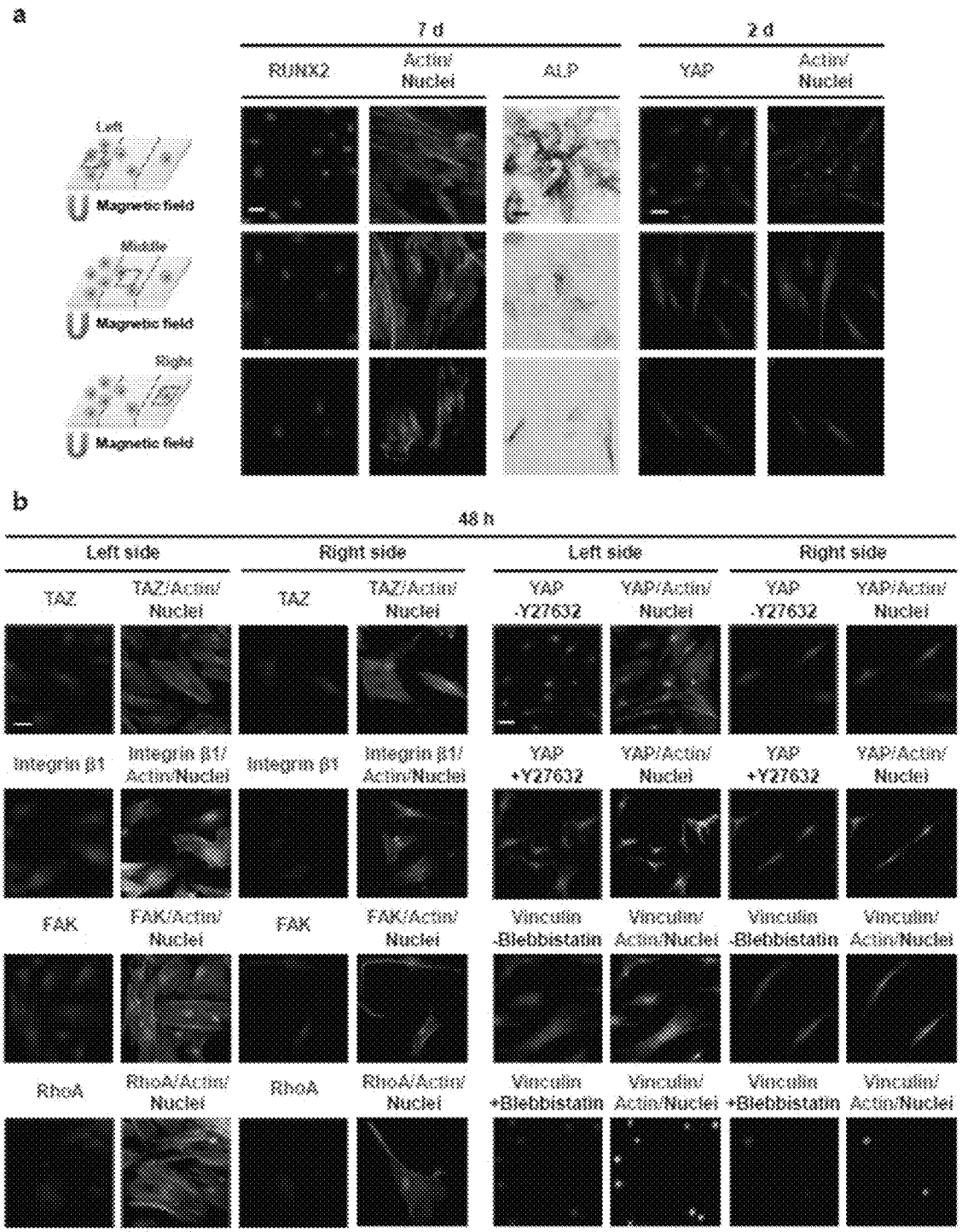

[FIG. 18]
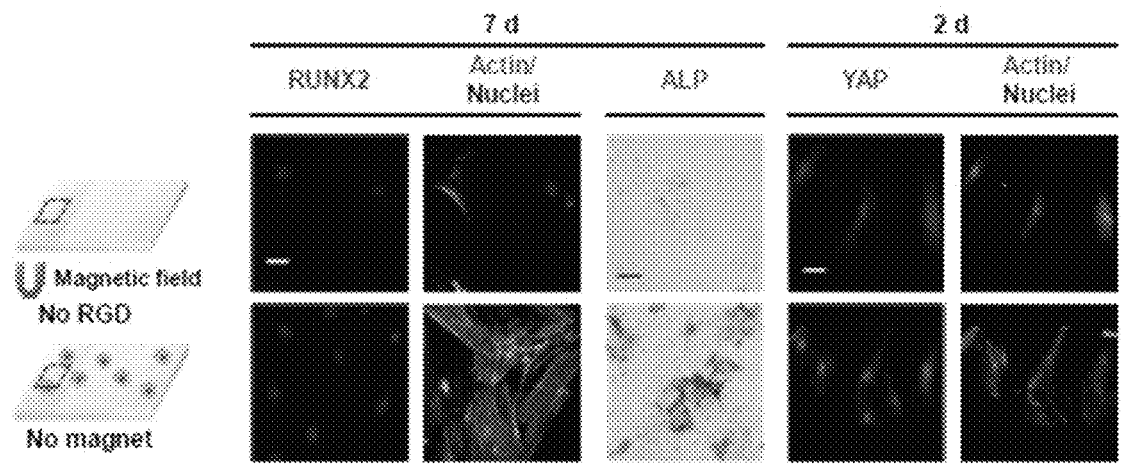
[FIG. 19]
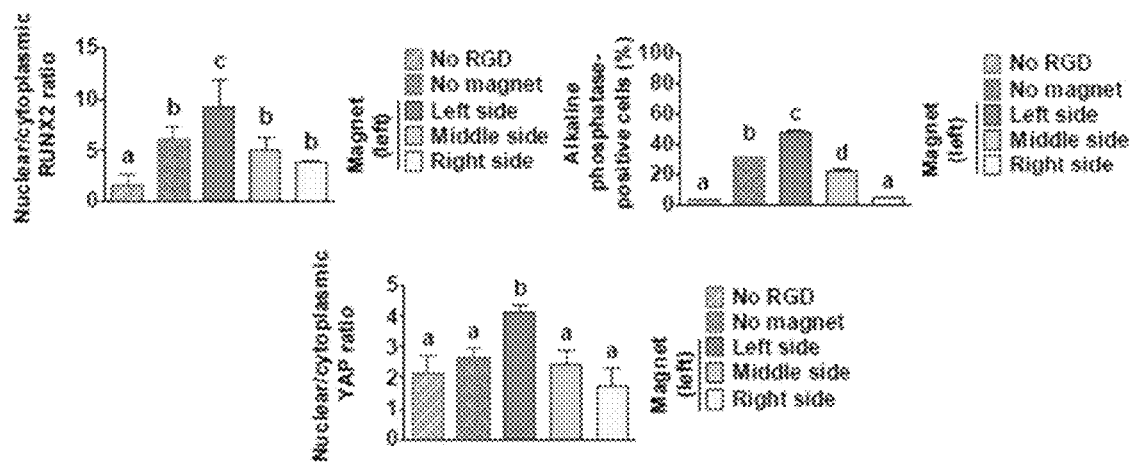

[FIG. 20]
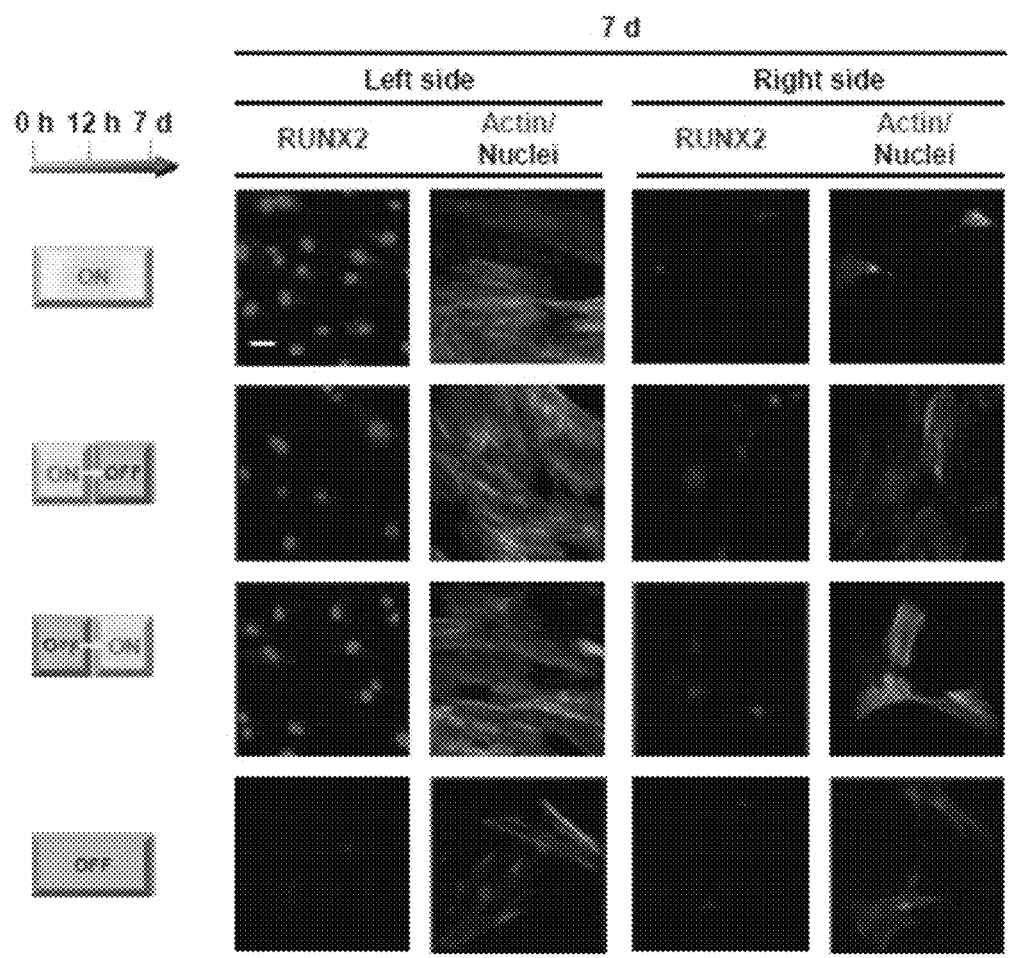
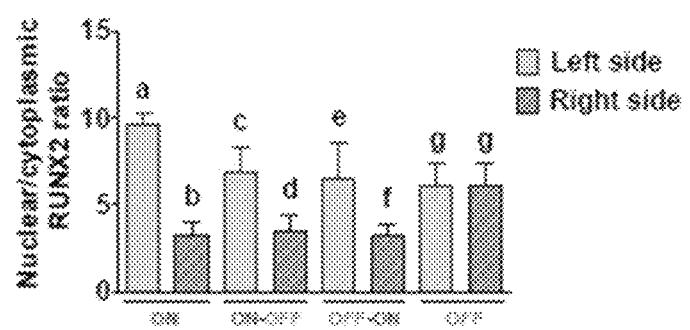

[FIG. 21]
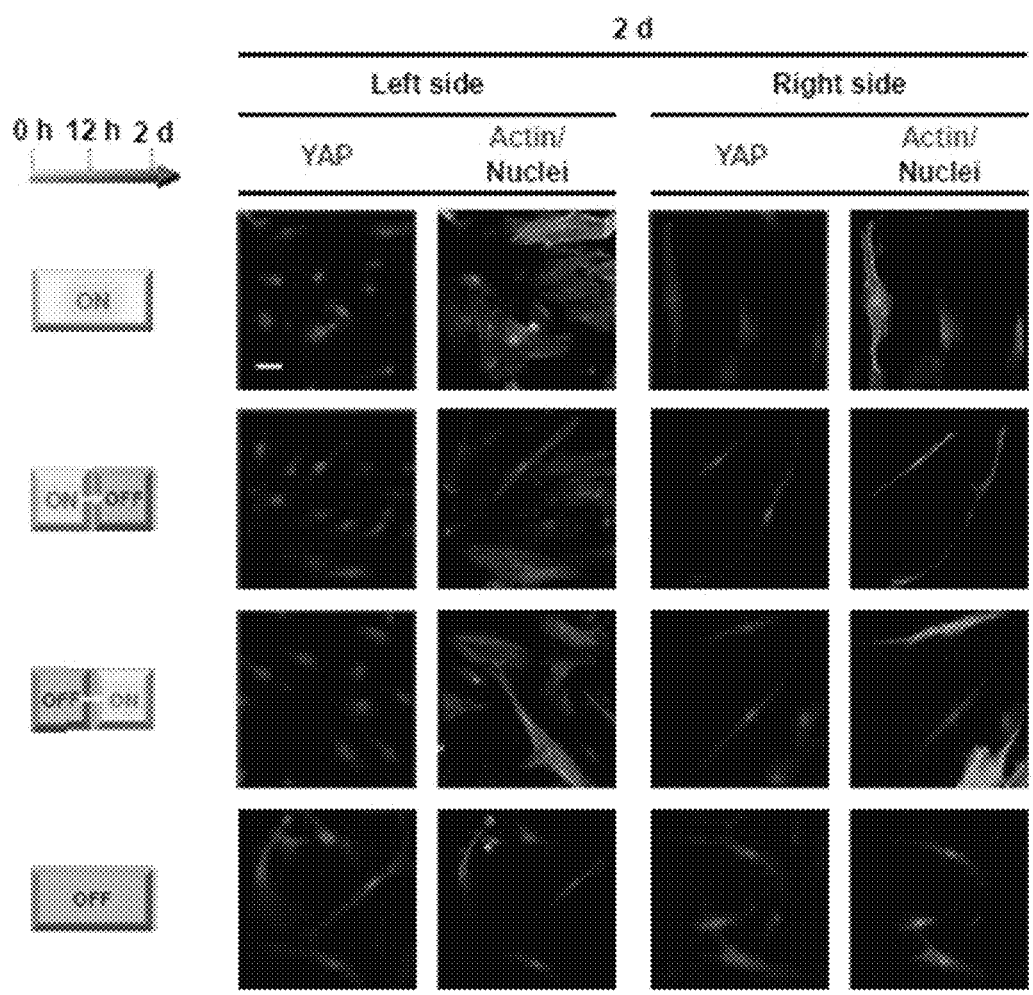
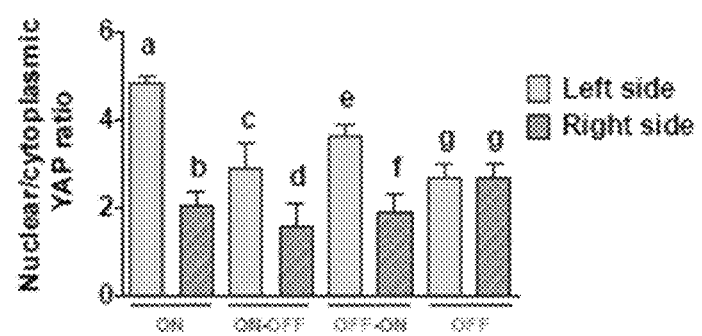

[FIG. 22]
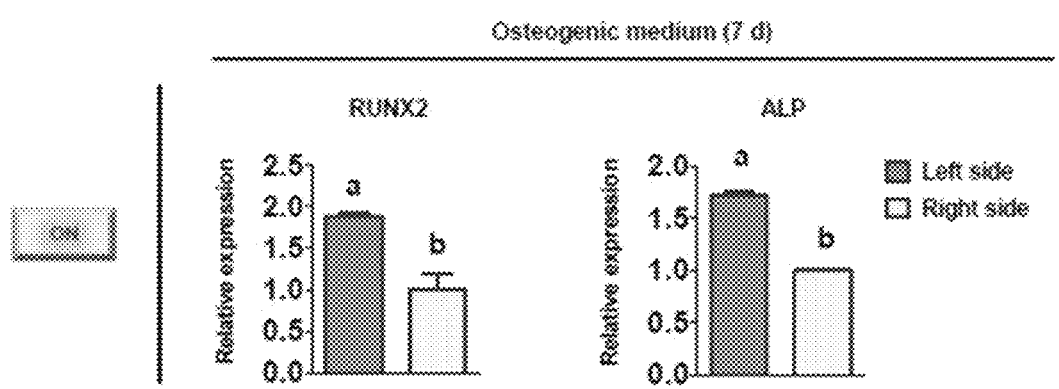

[FIG. 23]
a
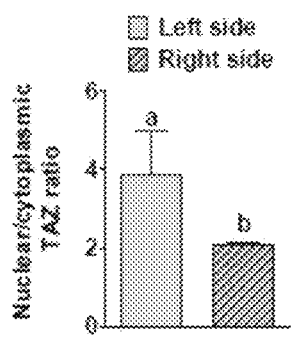
b
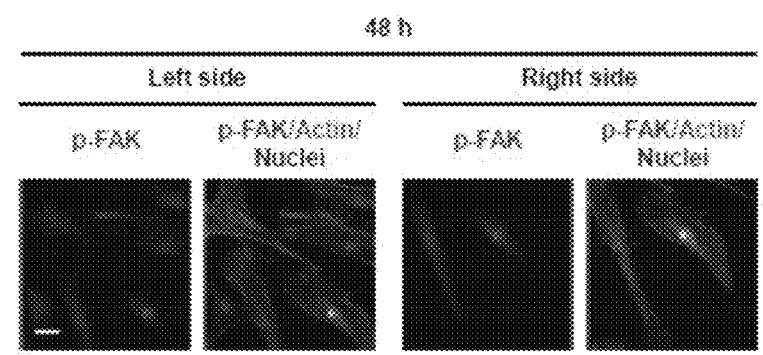
c
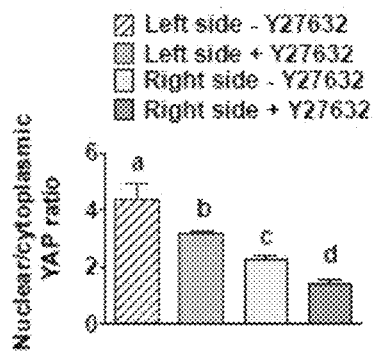
d
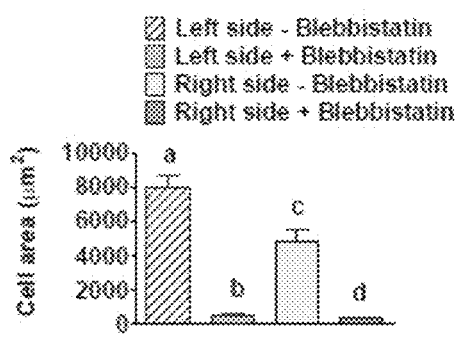

[FIG. 24]
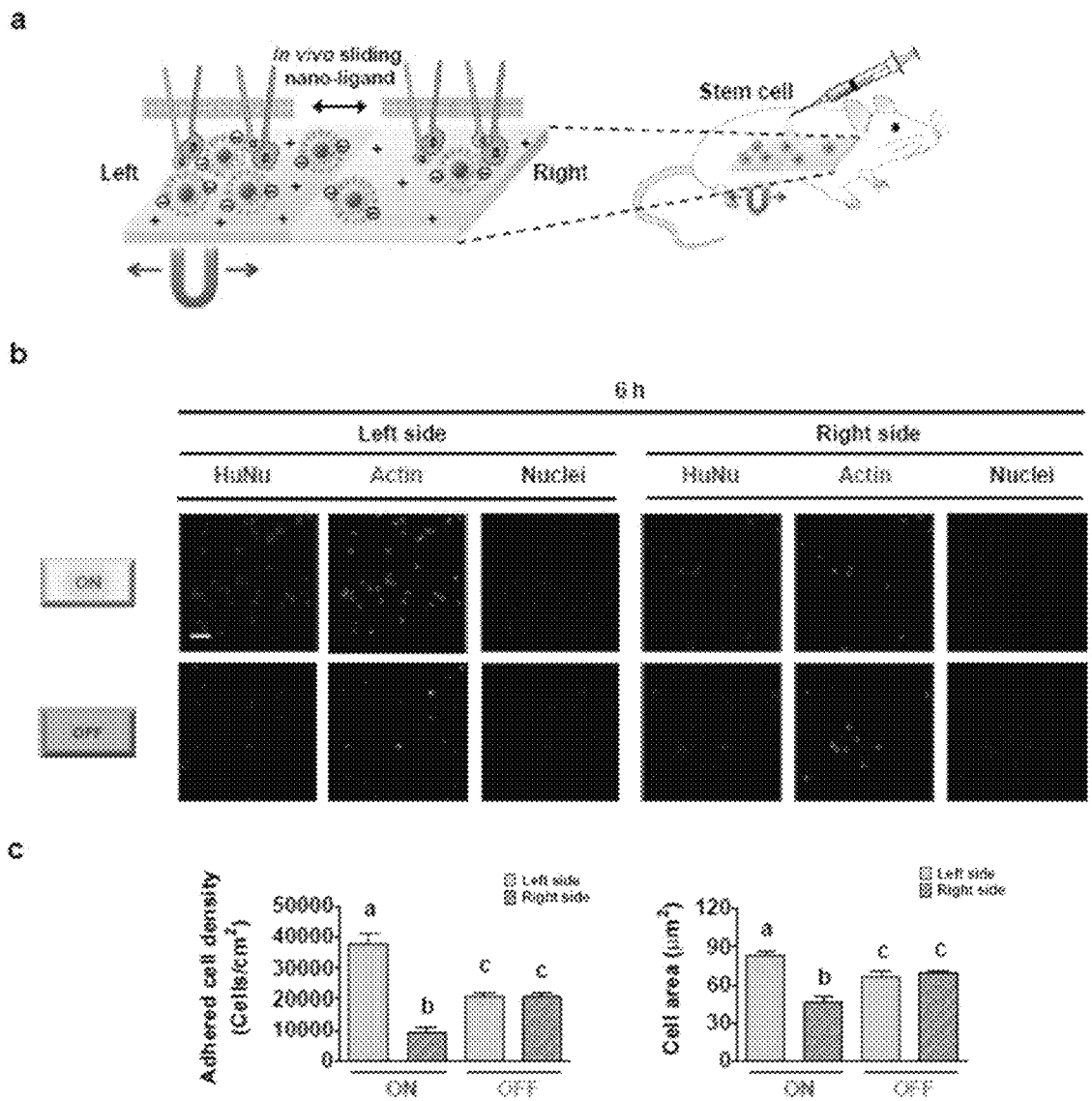

NANO-LIGAND FOR PROMOTING CELL ADHESION AND DIFFERENTIATION OF STEM CELLS AND METHOD OF PROMOTING CELL ADHESION AND DIFFERENTIATION OF STEM CELLS BY USING THE SAME

INCORPORATION BY REFERENCE OF SEQUENCE LISTING

The content of the electronically submitted sequence listing, file name: Q261742_sequence listing as filed.txt; size: 16,729 bytes; and date of creation: Nov. 23, 2022, filed herewith, is incorporated herein by reference in their entirety.

TECHNICAL FIELD

The present invention relates to a nano-ligand for promoting cell adhesion and differentiation of stem cells and a method of promoting cell adhesion and differentiation of stem cells by using the nano-ligand, and more particularly, to a method of remotely controlling adhesion and differentiation of stem cells by using the nano-ligand.

BACKGROUND ART

Stem cells can proliferate through self-renewal, and have the potential to differentiate into various cells, such as bone, fat, muscle, myocardium, blood vessels, and cartilage. Recently, in order to regenerate damaged tissues and organs by using these characteristics, many studies have been conducted on transplantation of stem cells or cells differentiated from stem cells. In addition, biomaterials that can help stem cells to differentiate into specific cells are also being actively studied.

As a method of efficiently controlling the regenerative effect of stem cells, a technology through the presentation of ligand in vivo is used. However, the existing presentation of nano-ligands in vivo is mostly static, and even though the presentation of nan-ligands in vivo is dynamic, it is impossible to reversibly change the macroscale ligand density through real-time remote control.

PRIOR ART LITERATURE

[Patent Document]
(Patent Document 1) Korean Patent Application Laid-Open No. 10-2018-0017704

SUMMARY OF THE INVENTION

In order to solve the aforementioned problems, the present invention provides a nano-ligand which is electrostatically coupled with a substrate and is movable, and a method of promoting adhesion and differentiation of stem cells by reversibly changing macroscale nano-ligand density through real-time remote control by using the nano-ligand.

An exemplary embodiment of the present invention provides a method of a nano-ligand for promoting cell adhesion and differentiation of stem cells, the nano-ligand including: a core including magnetic nano-particles; a coating layer provided to surround the core and including an integrin-binding ligand peptide; and a linker provided between the core and the coating layer, in which the integrin-binding ligand peptide is negatively charged.

Another exemplary embodiment of the present invention provides a method of preparing the nano-ligand for promoting cell adhesion and differentiation of stem cells, the method including: preparing a core including magnetic nano-particles; preparing a core coupled with a linker by mixing the core and a first suspension including a first linker; and mixing the core coupled with the linker and a second suspension including an integrin-binding ligand peptide (RGD).

Still another exemplary embodiment of the present invention provides a method of promoting cell adhesion and differentiation of stem cells, the method including: manufacturing a nano-ligand presenting substrate by putting a substrate, of which a surface is activated, in a solution including the nano-ligand for promoting adhesion and differentiation of stem cells; and controlling adhesion and differentiation of stem cells by treating the nano-ligand presenting substrate with stem cells and then applying an external magnetic field.

The nano-ligand for promoting cell adhesion and differentiation of stem cells according to the present invention has the form in which negatively charged ligands are coated on magnetic nanoparticles, and easily move on a substrate through electrostatic coupling with the substrate.

Further, the method of promoting cell adhesion and differentiation of stem cells according to the present invention may temporally and spatially, and reversibly control nano-ligand sliding by applying a magnetic field to a substrate including the nano-ligands, and efficiently control stem cell adhesion and differentiation ex vivo or in vivo through the magnetic-field based on spatiotemporal control.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 is a schematic diagram illustrating a nano-ligand for promoting cell adhesion and differentiation of stem cells and a method of promoting cell adhesion and differentiation of stem cells by using the same according to an exemplary embodiment of the present invention (CDDRGD: (SEQ ID NO: 1)).

FIG. 2 is a diagram illustrating the method of promoting cell adhesion and differentiation of stem cells according to the exemplary embodiment of the present invention (CDDRGD: (SEQ ID NO: 1)).

FIG. 3 is a Transmission Electron Micrograph (TEM) image of a slidable nano-ligand according to the exemplary embodiment of the present invention, and in this case, a scale bar indicates 20 nm.

FIG. 4 (a and b of FIG. 4) is a diagram illustrating a characteristic of the slidable nano-ligand according to the exemplary embodiment of the present invention. a of FIG. 4 is a dynamic light scattering image of a magnetic nanoparticles (MNPs) and amino-silica-coated MNPs with size distribution, and b of FIG. 4 is a High-Angle Annular Dark-Field Scanning Transmission Electron Microscopy (HAADF-STEM) image of representative amino-silica-coated MNP, and in this case, a scale bar indicates 20 nm.

FIG. 5 is a vibrating sample magnetometer hysteresis of the slidable nano-ligand according to the exemplary embodiment of the present invention.

FIG. 6 is a Fourier transform infrared spectra image of the slidable nano-ligand according to the exemplary embodiment of the present invention.

FIG. 7 is a diagram illustrating electrostatic coupling of the slidable nano-ligand to a substrate according to the exemplary embodiment of the present invention (CDDRGD: (SEQ ID NO: 1)).

FIG. 8 (a to e of FIG. 8) is an image photographed by Scanning Electron Microscopy (SEM) and Atomic Force Microscopy (AFM) of in situ reversible spatiotemporal manipulation of both macroscale and nanoscale nano-ligand sliding according to the exemplary embodiment of the present invention. a and b are images of a positively charged substrate and a nano-ligand, c and d are results of time-lapse SEM imaging, and e represents nanoscale displacement of nano-ligand sliding through AFM scanning.

FIG. 9 is an AFM image of in situ nano-ligand sliding in the absence of a permanent magnet of a Comparative Example.

FIG. 10 (a to c of FIG. 10) is a diagram illustrating modulation of integrin β1 binding of in situ control of a sliding nano-ligand according to the exemplary embodiment of the present invention. a of FIG. 10 is a schematic diagram of a sliding nano-ligand with a permanent magnet positioned under the "left" side of the substrate, b of FIG. 10 is an immunofluorescent confocal image of integrin β1 clusters bound to the sliding nano-ligand at the "left", "middle", and "right" sides of the substrate, and in this case, a scale bar indicates 50 μm, and c of FIG. 10 is a graph illustrating staining intensity of integrin β1 clusters at the "left", "middle", and "right" sides of the substrate.

FIG. 11 (a and b of FIG. 11) is an image representing a result of the in situ control experiment of the nano-ligand sliding according to the exemplary embodiment of the present invention. a of FIG. 11 is an immunofluorescent confocal image of a result of an investigation of whether integrin β1 ligation and focal adhesion of human mesenchymal stem cells (hMSCs) are controlled, and b of FIG. 11 is an immunofluorescent confocal image of a result of an investigation of whether time-regulated switching of the nano-ligand sliding is capable of tuning stem cell adhesion, and a scale bar indicates 50 μm.

FIG. 12 is a graph of a calculation of a density, an area, a focal adhesion number, and an aspect ratio of adherent cells after culturing hMSCs for 48 hours under a permanent magnet positioned under the "left" side of the substrate according to the exemplary embodiment of the present invention.

FIG. 13 (a and b of FIG. 13) is a diagram illustrating a result of an experiment of slidable nano-ligand mediated stem cell adhesion in the absence of an RGD ligand and permanent magnet of a Comparative Example. a of FIG. 13 is an immunofluorescent confocal image of the stem cells for vinculin, F-actin, and nuclei after culturing the stem cells for 48 hours without an RGD ligand or a permanent magnet, and b of FIG. 13 is a graph of a calculation of a density and area of adherent stem cells.

FIG. 14 is an immunofluorescent confocal image of the stem cells for time-regulated switching of macroscale nano-ligand presentation according to the exemplary embodiment of the present invention.

FIG. 15 is a graph of a calculation of a density, an area, and focal adhesion number of adhered cells for the temporal conversion of macroscale nano-ligand presentation according to the exemplary embodiment of the present invention.

FIG. 16 is a graph of a calculation of a density, an area, and an aspect ratio of adherent cells for spatiotemporally reversible conversion of the nano-ligand sliding according to the exemplary embodiment of the present invention.

FIG. 17 (a and b of FIG. 17) is an immunofluorescent confocal image of mechanosensing-mediated differentiation of the stem cells by in situ magnetic attraction of the slidable nano-ligands according to the exemplary embodiment of the present invention. a of FIG. 17 is an immunofluorescent image for RUNX2 and YAP with F-actin and nuclei and ALP expression in stem cells under a magnet. b of FIG. 17 is an immunofluorescent image for TAZ, integrin β1, FAK, and RhoA with F-actin and nuclei, YAP under ROCK inhibition (Y27632), and vinculin under myosin II inhibition (blebbistatin) in stem cells under a magnet condition.

FIG. 18 is an immunofluorescent confocal image of stem cells in the absence of RGD ligand and permanent magnet of a Comparative Example.

FIG. 19 is a graph illustrating a result of an experiment of mechanotransduction and differentiation of stem cells for magnetic attraction of the slidable nano-ligand according to the exemplary embodiment of the present invention, in which a nuclear to cytoplasmic RUNX2 fluorescence ratio, alkaline phosphatase-positive cells, and nuclear to a cytoplasmic YAP fluorescence ratio are calculated after culturing stem cells.

FIG. 20 (a and b of FIG. 20) is an immunofluorescent confocal image of an in situ time-regulated experiment of the nano-ligand sliding according to the exemplary embodiment of the present invention and a graph illustrating a calculation of a nuclear to cytoplasmic RUNX2 fluorescence ratio. a of FIG. 20 is an immunofluorescent confocal image for RUNX2, F-actin, and nuclei after culturing stem cells for 7 days with a permanent magnet positioned under the left side of the substrate ("ON") or removed from the substrate ("OFF"). b of FIG. 20 is a graph of a calculation of a nuclear to cytoplasmic RUNX2 fluorescence ratio.

FIG. 21 (a and b of FIG. 21) is a diagram illustrating a result of an experiment for mechanotranduction through time-regulated control of the slidable nano-ligand according to the exemplary embodiment of the present invention. a of FIG. 21 is an immunofluorescent confocal image for RUNX2, F-actin, and nuclei after culturing stem cells for 2 days with a permanent magnet positioned under the left side of the substrate ("ON") or removed from the substrate ("OFF"). "ON" and "OFF" conditions were continuously applied for 2 days (YAP) of culture or switched after 12-hour culturing. Stem cells were imaged at the center of the "left" and "right" side of the substrate. A scale bar indicates 50 μm. b of FIG. 21 is a graph of a calculation of a nuclear to YAP fluorescence ratio. Data is displayed as mean±standard errors (n=30). Statistically significant differences are indicated by different alphabets.

FIG. 22 is a diagram illustrating gene expression profiles of RUNX2 and ALP after culturing the stem cells for 7 days with a permanent magnet positioned under the "left" side of the substrate for the slidable nano-ligand according to the exemplary embodiment of the present invention.

FIG. 23 (a to d of FIG. 23) is a diagram illustrating a result of a calculation of magnetic attraction of the slidable nano-ligand according to the exemplary embodiment of the present invention based on the immunofluorescent image. a of FIG. 23 is a result of quantification of the nuclear to cytoplasmic TAZ fluorescence ratio from the immunofluorescent confocal image for TAZ illustrated in b of FIG. 17. b of FIG. 23 is an immunofluorescent confocal image for p-FAK with F-actin and nuclei. c of FIG. 23 is a graph illustrating a nuclear to cytoplasmic YAP fluorescence ratio under ROCK inhibition (with Y27632) and d of FIG. 23 is a graph illustrating a cell area under myosin II inhibition (with blebbistatin) illustrated in b of FIG. 4.

FIG. 24 (a to c of FIG. 24) is a diagram illustrating a result of an experiment of magnetic control of attracting the slidable nano-ligand according to the exemplary embodiment of the present invention based on the immunofluorescent image. a of FIG. 24 is a diagram illustrating an experiment of a magnetic control of nano-ligands, and b of FIG. 24 is an immunofluorescent image for human-specific HuNu with actin and nuclei of stem cells injected onto a slidable nano-ligand-presenting substrate after subcutaneous implantation with a magnet ("ON") or without a magnet ("OFF"). c of FIG. 24 is a graph illustrating quantification of in vivo adhered cell density and area.

DETAILED DESCRIPTION

Hereinafter, in order to describe the present invention in more specifically, an exemplary embodiment of the present invention will be described in more detail with reference to the accompanying drawings. However, the present invention is not limited to the exemplary embodiment described herein, and may also be specified in other forms.

A nano-ligand for promoting adhesion and differentiation of stem cells according to the present invention is a material having remote, spatiotemporal, and reversible controllability, and may mimic extracellular matrix (ECM) remodeling to regulate cell adhesion in vivo. Herein, the nano-ligand is a slidable nano-ligand with superparamagnetic nanomaterials amine-functionalized and conjugated with polyethylene glycol linker and negatively charged RGD ligand. In a method of promoting adhesion and differentiation of stem cells according to the present invention, electrostatic interaction is optimized in order to exhibit reversible slidability, the slidable nano-ligand is coupled to a positively charged substrate. Therefore, the present invention shows unprecedented imaging of both macroscale and in situ nanoscale nano-ligand sliding by magnetically attracting the slidable nano-ligand to manipulate a macroscale nano-ligand density. Further, the present invention shows that in situ magnetic control of attracting the slidable nano-ligand facilitates stem cell adhesion, both ex vivo or in vivo, with spatiotemporal and reversible control. Further, the present invention unravels that in situ magnetic attraction of the slidable nano-ligand stimulates mechanosensing-mediated differentiation of stem cells. The present invention may provide the method of promoting adhesion and differentiation of stem cells, which is excellent in regulating diverse reparative cellular processes in vivo through the remote control of ECM-mimicking spatiotemporal and reversible nano-ligand variations. The present invention provides a nano-ligand for promoting cell adhesion and differentiation of stem cells, including: a core including magnetic nanoparticles; a coating layer provided so as to surround the core and including an integrin-binding ligand peptide; and a linker provided between the core and the coating layer, in which the integrin-binding ligand peptide is negatively charged.

FIG. 1 is a schematic diagram illustrating a nano-ligand for promoting cell adhesion and differentiation of stem cells and a method of promoting cell adhesion and differentiation of stem cells by using the same according to the present invention.

Referring to FIG. 1, the nano-ligand of the present invention includes: a core including magnetic nanoparticles; and a coating layer coupled to a core and including an integrin-binding ligand peptide, in which the integrin-binding ligand peptide is a negatively charged integrin-binding peptide. In particular, the integrin-binding ligand peptide coupled to the core may have the form surrounding the core, like a micelle structure. Accordingly, a surface charge of the nano-ligand may represent a negative charge.

Further, FIG. 3 is a Transmission electron micrograph (TEM) image of the nano-ligand for promoting cell adhesion and differentiation of stem cells according to the exemplary embodiment of the present invention, and a size of the nano-ligand can be recognized. In particular, the nano-ligand may have a diameter of 30 to 60 nm. When the diameter of the nano-ligand is less than 30 nm, it is difficult to control a movement of the nano-ligand, and when the diameter of the nano-ligand is larger than 60 nm, adhesion efficiency of the stem cells may be degraded. In more particular, the nanobarcode may have a diameter of 30 nm to 50 nm, or 35 nm to 45 nm.

As long as the magnetic nanoparticles are nanoparticles having magnetic properties, the magnetic nanoparticles are not particularly limited. For example, the magnetic nanoparticle may have a diameter of 5 to 30 nm. When the diameter of the nanoparticle is less than 5 nm, the particle is too small, resulting in large loss and reducing efficiency, and when the diameter of the nanoparticle is larger than 30 nm, the diameter of the nano-ligand increases, resulting in degrading adhesion efficiency of stem cells. More particularly, the magnetic nanoparticle may have a diameter of 5 nm to 15 nm, or 10 nm to 20 nm. The nano-ligand of the present invention includes the magnetic nanoparticles, thereby promoting adhesion and differentiation of stem cells by using a magnetic field.

Further, in the magnetic nanoparticle, silica may be coated to a surface. In particular, in the magnetic nanoparticle, amino-silica may be coated to the surface. The kind of the silica may be any one or more of tetraethyl orthosilicate (TEOS) and (3-Aminopropyl)triethoxysilane (APTES).

For example, the nano-ligand of the present invention has a structure in which the core and the coating layer are connected by the linker, and the linker may be a polyethylene glycol (PEG)-based linker. In particular, the polyethylene glycol (PEG) linker may be maleimide-poly(ethylene glycol)-NHS ester (Mal-PEG-NHS ester). The present invention includes the linker, thereby improving coupling force between the core and the coating layer and improving durability of the nano-ligand.

The coating layer is coupled to the core or the linker coupled with the core, and has the form surrounding the core. In particular, the coating layer includes the integrin-binding ligand peptide (RGD), and the integrin-binding ligand peptide may have the negatively charged form and include a negatively charged thiolated integrin-binding ligand peptide. The present invention includes the negatively charged thiolated integrin-binding ligand peptide, so that the surface of the nano-ligand of the present invention has the negatively charged form, and accordingly, the nano-ligand may freely move on a substrate through the electrostatic coupling with the substrate. By the characteristic, the nano-ligand is also referred to as the "slidable nano-ligand", and may promote adhesion and differentiation of stem cells through sliding of the nano-ligand on the substrate.

Further, the present invention provides a method of preparing the nano-ligand for promoting cell adhesion and differentiation of stem cells, including: preparing a core including magnetic nanoparticles; preparing a core coupled with a linker by mixing the core and a first suspension including linker, and mixing the core coupled with the linker and a second suspension including an integrin-binding ligand peptide (RGD).

The preparing of the core may include forming the silane-coated core by stirring the magnetic nanoparticles with a silane solution. In particular, the preparing of the core may include forming an amino-silane coated core by stirring the magnetic nanoparticles with an amino-silane solution. The kind of the silane included in the silane solution may be any one or more of tetraethyl orthosilicate (TEOS) and (3-Aminopropyl)triethoxysilane (APTES).

In particular, the preparing of the core coupled with the linker may be performed by stirring the core in a suspension including the linker for 10 to 20 hours or 10 to 15 hours under the dark condition. Accordingly, the linker-coupled core may be obtained. In this case, the linker-coupled core may be obtained by washing the core with a solvent two or more times by using the permanent magnet. The solvent may contain any one or more of dimethylformaldehyde (DMF) and dimethyl sulfoxide (DMSO).

In this case, the linker may be a polyethylene glycol (PEG) linker. In particular, the polyethylene glycol (PEG) linker may be maleimide-poly(ethylene glycol)-NHS ester (Mal-PEG-NHS ester). By coupling the linker to the core, it is possible to improve coupling force between the core and the coating layer and improve durability of the nano-ligand.

Further, the mixing of the core with the second suspension may be performed by stirring the core coupled with the linker in a suspension including the integrin-binding ligand peptide (RGD) for 10 to 20 hours or 10 to 15 hours under the dark condition. In this case, the magnetic nanoparticles (nano-ligands) coupled with the negatively charged integrin-binding ligand peptide may be obtained by using the solvent using the permanent magnet. The solvent may contain any one or more of dimethylformaldehyde (DMF) and dimethyl sulfoxide (DMSO).

Herein, the coating layer may be formed on the core through the process of stirring the integrin-binding ligand peptide. In particular, the integrin-binding ligand peptide may be the negatively charged form, and may be the negatively charged thiolated integrin-binding ligand peptide. The coating layer is formed on the core with the negatively charged integrin-binding ligand peptide, so that the surface of the nano-ligand of the present invention may have the negatively charged form, resulting in the free movement of the nano-ligand on the substrate through the electrostatic coupling with the substrate. By the characteristic, the nano-ligand is also referred to as the "slidable nano-ligand", and may promote adhesion and differentiation of stem cells through sliding of the nano-ligand on the substrate.

Further, the present invention provides a method of promoting cell adhesion and differentiation of stem cells, including: manufacturing a nano-ligand presenting substrate by putting a substrate, of which a surface is activated, in a solution including the nano-ligand for promoting adhesion and differentiation of stem cells; and controlling adhesion and differentiation of stem cells by treating the nano-ligand presenting substrate with stem cells and then applying an external magnetic field.

FIGS. 1 and 2 are diagrams illustrating the method of promoting cell adhesion and differentiation of stem cells according to the exemplary embodiment of the present invention. Referring to FIGS. 1 and 2, it can be seen that the nano-ligand, of which the surface is negatively charged, is electrostatically coupled onto the positively charged substrate, following by a magnetic field, so that adhesion and differentiation of stem cells are promoted or activated in the part to which the magnetic field is applied. In particular, the substrate and the nano-ligand are coupled through the electrostatic coupling, so that the nan-ligand moves (slides) along the location to which the magnetic field is applied, and thus it is possible to promote adhesion and differentiation of stem cells in a desired region by regulating a density of the nano-ligand in the portion to which the magnetic field is applied.

In particular, the manufacturing of the nano-ligand presenting substrate includes: soaking the surface of the substrate in an acid solution; activating the surface of the substrate by putting the soaking-completed substrate in an amino-silane solution; and treating the activated substrate by using ultrasonic waves at a room temperature. The soaking of the surface of the substrate in the acid solution may include soaking the surface of the substrate in an acid solution containing any one or more of hydrochloric acid and sulfuric acid for 30 minutes to 2 hours or 30 minutes to 1 hour. Through this, bonding with an amino group is facilitated by bonding a hydroxyl group to the surface of the substrate, thereby effectively performing activation of the surface of the substrate.

The activating of the surface of the substrate may include activating the surface of the substrate by putting the substrate in the amino-silane solution under the dark condition. The amino-silane solution may include (3-aminopropyl) triephoxysilane (APTES). In this case, the activation of the surface of the substrate means that the surface of the substrate is positively charged, and particularly, the surface of the substrate may be activated by binding an amine group onto the substrate. The surface of the substrate is positively charged by activating the surface of the substrate by soaking the substrate in the amino-silane solution, so that the substrate may be coupled with the nano-ligand by electrostatic attraction.

Further, the treating of the activated substrate by using ultrasonic waves may include manufacturing the nano-ligand presenting substrate by putting the substrate, of which the surface is activated, in the solution including the nano-ligand. In particular, the treating of the activated substrate by using ultrasonic waves was performed by putting the substrate, of which the surface is activated, in the solution including the nano-ligand under ultrasonic-wave treatment in purified water for 30 minutes to 2 hours or 30 minutes to 1 hour at a room temperature.

The controlling the adhesion and differentiation of the stem cells may be performed by positioning the nano-ligand presenting substrate in vivo or ex vivo and then applying a magnetic field of 100 to 700 mT for 12 to 48 hours. In particular, the controlling the adhesion and differentiation of the stem cells may be performed by positioning the nano-ligand presenting substrate in vivo or ex vivo and then applying a magnetic field of 100 to 600 mT, 200 to 600 mT, or 300 to 550 mT for 12 to 36 hours, 24 to 26 hours, or 12 to 24 hours. By applying the magnetic field to the nano-ligand presenting substrate, it is possible to promote adhesion of stem cells to the nano-ligand located on the substrate, and also promote differentiation of the adherent stem cells.

Further, the controlling the adhesion and differentiation of the stem cells may be performed by changing the location in the substrate to which the magnetic field is applied. In particular, the adhesion and differentiation of the stem cells may be spatially controlled by changing the location in the substrate, to which the magnetic field is applied, while applying the magnetic field of 100 to 600 mT, 200 to 600 mT, or 300 to 550 mT. For example, it is possible to promote the adhesion and differentiation of the stem cells only in a desired portion of the substrate by regulating the density of nano-ligands on the substrate by applying the magnetic field to a part of the substrate.

In addition, the controlling the adhesion and differentiation of the stem cells may be performed by changing the location of the magnetic field applied to a lower end of the substrate over time. In particular, the adhesion and differentiation of the stem cells may be temporally and spatially controlled by changing the location in the substrate to which the magnetic field is applied over time while applying the magnetic field of 100 to 600 mT, 200 to 600 mT, or 300 to 550 mT. More particular, it is possible to control the degree of promotion of the adhesion and differentiation of the stem cells in each portion on the substrate by regulating the density of the nano-ligands located on the substrate over time by individually applying the magnetic field to each portion of the substrate. For example, in the case where the magnetic field is applied to the left side of the substrate for 12 to 24 hours and the magnetic field is applied to the right side of the substrate for 24 to 36 hours, the amount of stem cells adhered to the left side and the right side of the substrate or differentiated may be varied.

Hereinafter, examples of the present invention will be described. However, the examples below are merely preferable examples of the present invention, and the scope of the present invention is not limited by the examples.

PREPARATION EXAMPLE

Preparation Example 1

Prepare Slidable Nano-Ligand
1) Prepare Magnetic Core (MNP)
For in situ reversible control of a slidable nano-ligand, a magnetic core of a slidable nano-ligand was prepared as described below. About 80 mL of ethanol, 60 mL of deionized (DI) water, and 140 mL of heptane were first mixed. To this mixture, 36.5 g (120 mmol) of sodium oleate and 10.8 g (40 mmol) of iron (III) chloride hexahydrate were added at 70° C. for 4 hours under an inert environment. After the completed mixing, a heptane layer containing an iron-oleate was separately collected. After washing with DI water, heptane was evaporated. About 5.7 g (20 mmol) of oleic acid and 200 g of 1-octadecene were mixed, to which 36 g (40 mmol) of the dried iron-oleate was added. This mixture solution was maintained at 100° C. for approximately 5 minutes and subsequently at 320° C. for approximately 30 minutes. Following the reaction, the mixture solution was cooled to room temperature, washed with ethanol three times with the collection using a permanent magnet, and then dispersed in heptane for the storage of the magnetic core.

2) Functionalization of Amino-Silica of Magnetic Core (Amino-Silica Coated MNP)
Approximately 30 mg of magnetic core nanoparticle in heptane was dispersed in 25 mL of cyclohexane, to which 5 mL of Triton-X, 5 mL of 1-hexanol, 0.5 mL of $NH_4OH$, and 1 mL of DI water were serially added. This mixture solution was stirred for 30 minutes to stabilize the emulsion. To the emulsion, 12.5 μL of tetraethyl orthosilicate (TEOS) was slowly added and stirred for 10 minutes. Then, 6.25 μL of (3-Aminopropyl)triethoxysilane (APTES) was added to this emulsion and stirred for 16 hours. Following the reaction, 25 mL of acetone was rapidly added to the emulsion, which was washed with acetone and DMF using a permanent magnet to collect the nanoparticle. The amino-silica coated MNP was dispersed in 1 mL of DMF.

3) Prepare Slidable Nano-Ligand
In order to complete a nano-assembly of the slidable nano-ligand, the amino-silica coated MNP was serially grafted with polyethylene glycol (PEG) linker, to enhance the slidability of nano-ligand, and subsequently grafted with negatively charged RGD ligand. The PEG linker also served to prevent cellular uptake. Approximately 20 mg of amino-silica coated MNP in 1 mL of DMF was added to 5 mg of maleimide-poly(ethylene glycol)-NHS ester (Mal-PEG-NHS ester; $M_n$=5000 Da, Biochempeg), to which 2 μL of N,N-Diisopropylethylamine (DIPEA) was added. The suspension was stirred for 16 hours under dark condition and then washed with DMF and DMSO (three times each) by using a permanent magnet. The PEGylated amino-silica coated MNP in 1 mL of DMSO was added to 0.5 mg of negatively charged thiolated RGD peptides (CDDRGD (SEQ ID NO: 1), GL Biochem), to which 0.2% DIPEA and 10 mM Tris(2-carboxyethyl)phosphine hydrochloride (TCEP) were subsequently added. The mixture solution was stirred for 16 hours under dark conditions, washed with DMSO three times with the collection using a permanent magnet, and then kept in DMSO prior to their electrostatic coupling to the substrate.

Comparative Preparation Example 1

A "No RGD" nano-ligand was prepared by the same method as that of Preparation Example 1 except that a negatively charged thiolated RGD peptide (CDDRGD (SEQ ID NO: 1), GL Biochem) was not added.

Example

Example 1

Slidable Nano-Ligand and Coupling of Slidable Nano-Ligand with Substrate
In order to reversibly couple the slidable nano-ligand prepared in the Preparation Example to the substrate, culture-grade glass coverslips (22 mm×22 mm) were used. The glass substrates were aminated to present positive charges prior to the coupling of the negatively charged slidable nano-ligand. The substrates were soaked in the 1:1 mixture of hydrochloric acid and methanol for 30 minutes to remove any organic impurities and then washed with DI water three times. The substrates were then soaked in sulfuric acid for 1 hour to activate the hydroxyl functional group on the surface and were then washed with DI water three times. The activated substrates were treated with 1:1 mixture of APTES and ethanol for 1 hour under dark conditions to functionalize the substrates to present amine group. The amino-functionalized substrates were washed with ethanol three times and dried at 100° C. for 1 hour. The suspension of the slidable nano-ligand in DMSO was diluted in 1:20 with DMSO and then added to the positively charged amino-functionalized substrate. The slidable nano-ligand was allowed for electrostatic coupling to the substrate at a room temperature for 1 hour under the ultrasonic treatment and then washed with DMSO three times and DI water three times to obtain the substrate presenting the slidable nano-ligand.

Experimental Example

Experimental Example 1

In order to check the form of the slidable nano-ligand according to the present invention, Transmission Electron Micrograph (TEM), dynamic light scattering, and High-Angle Annular Dark-Field Scanning TEM (HAADF-STEM) analysis were performed on the slidable nano-ligand, and the result of the analysis is represented in FIGS. 3 and 4.

Further, in order to check the property and a chemical bonding characteristic of the slidable nano-ligand, Vibrating-Sample Magnetometry and Fourier Transform Infrared Spectroscopy (FTIR) were performed on the slidable nano-ligand, and the result thereof is represented in FIGS. 5 and 6.

In particular, in the TEM experimental, TEM imaging was performed by using Tecnai 20 (FEI, USA) in order to check a size and a shape characteristic of the slidable nano-ligand.

Further, High-Angle Annular Dark-Field Scanning Transmission Electron Microscopy (HAADF-STEM) is to characterize the size and shape characteristic of the representative slidable nano-ligand, and HAADF-STEM imaging was carried out by using JEOL 2100F with 1 nm probe size, 20 µm condenser aperture, and 80 to 150 mrad collection angle for Z contrast.

In addition, in Dynamic Light Scattering (DLS) analysis, in order to quantify the size distribution profile (hydrodynamic diameter) in the assembly process of sliding nano-ligand, DLS measurement (Zetasizer Nano ZS90 Malvern Panalytical, Malvern, UK) was carried out.

Further, the FT-IR was carried out by using GX1 (Perkin Elmer Spectrum, USA) in order to confirm the serial chemical changes in the modification of slidable nano-ligand. The samples subjected to the analysis of changes in chemical bond characteristics were lyophilized and densely packed into KBr pellet prior to the analysis.

In order to characterize the reversible slidable (superparamagnetic) property of the nano-ligand, the magnetic core in the slidable nano-ligand was subjected to the VSM measurement (EV9; Microsense) at a room temperature under the applied magnetic field. The corresponding magnetic moment was presented in a hysteresis loop after normalization to the dry weight with the magnetic core in the slidable nano-ligand.

FIG. 3 is a Transmission electron micrograph (TEM) image of a nanoscale image of the slidable nano-ligand and in this case, a scale bar indicates 20 nm. a of FIG. 4 is a result of dynamic light scattering of magnetic nanoparticles (MNPs) and amino-silica-coated MNPs with size distribution, and b of FIG. 4 is an HAADF-STEM image of the amino-silica-coated MNP, and in this case, a scale bar indicates 20 nm.

Referring to FIGS. 3 and 4, it was confirmed the homogeneous spherical shape of slidable nano-ligands around 40±5 nm.

FIG. 5 is a vibrating sample magnetometer hysteresis of the slidable nano-ligand and FIG. 6 is a Fourier transform infrared spectra image of the slidable nano-ligand according to the exemplary embodiment of the present invention. In particular, FIG. 6 is the Fourier transform infrared spectra image of the MNP, the silica-coated MNP, and the RGD ligand-presenting PEG grafted silica-coated MNP (RGD-PEG-silica-coated MNP, slidable nano-ligand).

Referring to FIG. 5, the result of the analysis confirmed the superparamagnetic property of 20 emu/g Ms. Through this, the slidable nano-ligand according to the present invention exhibits the superparamagnetic property to be reversibly slidable, so that the superparamagnetic property is very important to magnetically manipulating the sliding of the nano-ligand temporally and reversibly.

Referring to FIG. 6, Fe—O binding was detected at the absorption peak value of 699 $cm^{-1}$ in superparamagnetic iron oxide core nanoparticles. Si—O binding was detected at the absorption peak value of 1168 $cm^{-1}$ in the silica shell. In the slidable nano-ligand, the PEG linker ($M_n$=5,000 Da) improve the sliding property and inhibits uptake by cells as demonstrated in previous literature, and CDDRGD (SEQ ID NO: 1) represented C=O bonding at the absorption peak of 1152 $cm^{-1}$ and amide bonding at the absorption peak of 1635 $cm^{-1}$. The FTIR analysis confirmed the successful assembly of the slidable nano-ligand.

Experimental Example 2

In order to verify in situ reversible spatiotemporal control of the slidable nano-ligand according to the present invention, the slidable nano-ligand was photographed with the SEM, and AFM imaging was carried out, and the result thereof is represented in FIGS. 8 and 9.

In particular, as illustrated in FIG. 7, in order to electrostatically control the macroscale nano-ligand presentation, in the present invention, the slidable ligand was coupled to the positively charged substrate for in situ spatiotemporally controlling the sliding of the nano-ligand. Through the electrostatic coupling of the nano-ligand and the substrate, reversible movement of the sliding of the nano-ligand was allowed.

Herein, in order to confirm the characteristics of the electrostatic coupling of the slidable nano-ligand to the substrate and the in situ reversible and spatiotemporal control of macroscale nano-ligand presentation, the SEM imaging (FE-SEM, FEI, Quanta 250 FEG) was carried out. The substrate was dried and platinum-coated using a sputter coater. The density of the substrate-coupled slidable nano-ligand was calculated by Image J software from 10 different images and shown as mean±standard errors. For in situ reversible and spatiotemporal control of macroscale ligand density, a permanent magnet (270 mT) was positioned under the left side of the substrate for 12 hours, re-positioned under the right side for 12 hours, and then positioned under the left side. The spatiotemporal changes in the macroscale ligand density were measured, and the result of the measurement is represented in FIG. 8.

Further, in order to confirm the characteristics of in situ 2 and 3D images of slidable nano-ligand on the substrate, in situ magnetic Atomic Force Microscopy (AFM) imaging (Asylum Research, XE-100 System) was carried out. The imaging was carried out in AC in air mode at 25° C. by using AFM cantilever (Nanosensors, SSS-SEIHR-20) with a spring constant of 5-3 N/m and a resonance frequency of 96-175 kHz. AFM imaging was serially conducted on the identical scanning area in the absence and presence of the magnet under the opposite side of the scanning area to characterize in situ nanoscale motion of slidable nano-ligand. As a comparative example experiment, serial AFM imaging on the identical scanning areas in continuous absence of the magnet was performed to characterize negligible nanoscale movement of the slidable nano-ligand by serial AFM scanning, and a result thereof is represented in FIGS. 8 and 9.

FIG. 8 is an image for in situ reversible spatiotemporal manipulation of sliding of macroscale and nanoscale nano-ligands. Referring to a and b of FIG. 8, the positively charged amino-functionalized substrate was optimally and homogeneously coupled with negatively charged slidable nano-ligand as evidenced by the SEM and the 3D AFM. Further, a macroscale nano-ligand density was calculated to be approximately 17±3 nano-ligand particles per $\mu m^2$. The present invention uses the macroscale ligand density because it was optimal in in situ spatiotemporal control of nano-ligand sliding without the aggregation of slidable nano-ligand, thereby allowing reversible motion of nanoligand, which significantly altered focal adhesion and mechanotransduction of stem cells.

c and d of FIG. 8 are results of the SEM imaging of the spatiotemporal control experiment, and a permanent magnet was positioned under the left side of the substrate to attract the slidable nano-ligand toward the left side, switched to the right side, and reverted to the left side each 12 hours. Time-lapse SEM imaging revealed the significantly higher nano-ligand particle density at the left, right, and left sides at 12 hours, 24 hours, and 36 hours, respectively, thereby confirming complete spatiotemporal reversibility of the nano-ligand sliding.

e of FIG. 8 is a comparative example of the spatiotemporal control experiment, and shows nanoscale displacement of nano-ligand sliding through serial in situ magnetic AFM scanning on the identical area with and without the magnet at the opposite side of the scanning area. In e of FIG. 8, the slidable nano-ligands were clearly identified without magnet, and moved away along the magnet.

FIG. 9 is a comparative example experiment, and is an in situ AFM image of the nano-ligand sliding in the absence of the magnet in the identical scanning. Referring to FIG. 9, black dotted lines are illustrated along the slidable nano-ligands in two different images. A scale bar indicates 50 nm. In the absence of the magnet, the serial AFM imaging in the identical scanning area confirmed the negligible nanoscale movement of the slidable nano-ligand.

Experimental Example 3

In the remote control method by using the slidable nano-ligand according to the present invention, in order to confirm the effect of the spatiotemporal reversible tuning of the macroscale nano-ligand presentation on the control of the adhesion of the stem cells, whether the in situ control of the nano-ligand sliding is capable of modulate integrin β1 ligation and focal adhesion of human mesenchymal stem cells (hMSCs) was investigated.

The binding experiment of integrin β1 to the slidable nano-ligand was carried out as described below. In order to evaluate binding efficiency of integrin β1 to in situ sliding nano-ligand, the sliding nano-ligand-presenting substrate was incubated in 50 μg/mL of integrin β1 in phosphate-buffered saline (PBS) at 4° C. for 12 hours with a permanent magnet positioned under the "left" side of the substrate. The incubated substrate was fixed with 4% (w/v) paraformaldehyde at a room temperature for 10 minutes and immunofluorescently stained against integrin β1 (Santa Cruz Biotechnology) to examine integrin β1 bound to the sliding nano-ligand, and the result thereof is represented in FIG. 10.

Further, the experiment of the in vitro regulation of the adhesion and differentiation of the stem cells under in situ control of the nano-ligand sliding was carried out as described below. In order to investigate the effect of nano-ligand sliding in situ on the adhesion of stem cells, the substrate including the slidable nano-ligand of the present invention was sterilized with UV light and then blocked with 1% bovine serum albumin (BSA, Sigma-Aldrich) at 37° C. for 1 hour to minimize non-specific cell adhesion. Human mesenchymal stem cells (hMSCs, passage 5, Lonza) were plated on the treated substrate at a density of 5000 cells/cm$^2$ and cultured in a basal medium containing high glucose DMEM, 10% (v/v) fetal bovine serum, 4 mM L-glutamine, and 50 U/mL penicillin/streptomycin at 37° C. and 5% $CO_2$. The adhesion of stem cells was investigated with a permanent magnet (270 mT) positioned under the "left" side of the substrate to promote sliding of the nano-ligand toward the left side. The adhered stem cells were imaged at the center of various sides (left, middle, and right sides) of the substrate, and a result thereof is represented in FIGS. 11 and 12.

FIG. 10 is a diagram illustrating modulation of integrin β1 binding of in situ control of the sliding nano-ligand. a of FIG. 10 is a schematic diagram illustrating the sliding nano-ligand with a permanent magnet positioned under the "left" side of the substrate, and b of FIG. 10 is confocal images of immunofluorescence for integrin β1 clusters bound to the sliding nano-ligand at the "left", "middle", and "right" side of the substrate, which are indicated by red arrows, and in this case, a scale bar indicates 50 μm. c of FIG. 10 is a graph of a calculation of staining intensity of the integrin β1 clusters at the "left", "middle", and "right" side of the substrate. Data is shown as mean±standard errors (n=30). Different alphabet letters were assigned to the compared groups with statistically significant differences.

FIG. 11 is an image representing a result of the in situ control experimental of the nano-ligand sliding according to the exemplary embodiment of the present invention, and illustrates that spatiotemporal reversible attraction of the slidable nano-ligand promotes the adhesion of the stem cells. FIG. 11 is an immunofluorescent image for vinculin, F-actin, and nuclei in stem cells under (a) a static position or (b) a switching positions of the magnet. A scale bar indicates 50 μm.

FIG. 12 is a graph of a calculation of the density, area, focal adhesion number, and aspect ratio of adherent cells after 48 hours of culturing hMSCs under a permanent magnet positioned under the "left" side of the substrate, and the in situ manipulation of the macroscale ligand presentation by the attraction of the sliding nano-ligand promotes the focal adhesion of the stem cells. The calculation was performed by using the immunofluorescent confocal image illustrated in a of FIG. 3, and data is shown as mean±standard errors (n=30). Different alphabet letters were assigned to the compared groups with statistically significant differences.

Referring to a to c of FIG. 11 and FIG. 12, upon magnetic attraction of the slidable nano-ligand, immunofluorescent staining revealed significantly higher ligation efficacy of integrin β1 and stem cell adhesion with higher density and focal adhesion with more spread morphology, including pronounced vinculin expression in FA complexes on the left side (magnet side).

Further, as a comparative experiment, the nano-ligand of Comparative Preparation Example 1 was experimented on the substrate with the magnetic field ("No RGD" group), and the nano-ligand of Preparation Example 1 was experimented on the substrate with no magnetic field ("No magnet" group), and the result is represented in FIG. 13.

FIG. 13 is a diagram illustrating a result of an experiment of slidable nano-ligand mediated stem cell adhesion in the absence of an RGD ligand and permanent magnet of a Comparative Example, and a of FIG. 13 is an immunofluorescent confocal image of the stem cells for vinculin, F-actin, and nuclei after culturing the stem cells for 48 hours without an RGD or a permanent magnet. The adherent stem cells were imaged at the center of the "left", "middle", and "right" sides of the substrate. A scale bar indicates 50 μm. b of FIG. 13 is a graph of a calculation of a density and area of adherent stem cells and data is displayed as mean t standard errors (n=30). Same alphabets signify non-statistical differences amongst the compared groups.

Referring to FIG. 13, the nano-ligand-sliding-mediated regulation of stem cell adhesion was ineffective for the "No RGD" and "No magnet" groups whereas the "No RGD"

group showed minimal non-RGD-specific adhesion of stem cells by efficient blocking. Through this, it is possible to recognize that the RGD ligand and the magnetic field (permanent magnet) are necessary for in situ control of the slidable nano-ligand-mediated stem cell adhesion.

Further, whether time-regulated switching of the nano-ligand sliding of the slidable nano-ligand according to the present invention can tune stem cell adhesion was investigated.

The effect of the time-regulated switching of the macroscale nano-ligand presentation on the adhesion of the stem cells was investigated by switching "ON" and "OFF", that is, by placing the permanent magnet under the left side of the substrate ("ON") or removing the permanent magnet from the substrate ("OFF"). The effect of the spatiotemporal reversible modulation of the nano-ligand sliding on the adhesion of the stem cells was investigated by switching the location of the permanent magnet between two opposite sides, that is, under the "left side" to the "right side" and then to the "left side" of the substrate.

FIG. 14 is an immunofluorescent confocal image of the stem cells for time-regulated switching of the macroscale nano-ligand presentation according to the exemplary embodiment of the present invention. In particular, FIG. 14 is an immunofluorescent confocal image of the stem cells for vinculin, F-actin, and nuclei after culturing the stem cells for 12 hours or 48 hours with a permanent magnet positioned under the left side of the substrate ("ON") or removed from the substrate ("OFF") for left (magnet side) and right (non-magnet side) side. "ON" and "OFF" conditions were continuously applied for 48 hours of culture or switched at 12 hours after culture. The images were acquired at the center of the left side of the substrate. A scale bar indicates 50 μm. Through this, it can be seen that the slidable nano-ligand of the present invention controls adhesion of the stem cells through the macroscopic time-regulated switching.

FIG. 15 is a graph of a calculation of the density, area, and focal adhesion number of adherent cells for the temporal switching of the macroscale nano-ligand presentation in the exemplary embodiment of the present invention. In particular, the density, area, and focal adhesion number of adherent cells at the left side of the substrate were calculated after 12 hour or 48 hour of culturing stem cells with a permanent magnet positioned under the left side of the substrate ("ON") or removed from the substrate ("OFF"). "ON" and "OFF" conditions were continuously applied for 48 hours of culture or converted at 12 hours after culture. The calculations were made by using the immunofluorescent confocal images for the left (magnet side) and right (non-magnet side) sides illustrated in FIG. 14, and data is shown as mean±standard errors (n=30). Different alphabet letters were assigned to the compared groups with statistically significant differences.

Referring to FIGS. 14 and 15, a permanent magnet was placed under the left side of substrate ("ON") or was not placed near the substrate ("OFF") for 48 hours. Furthermore, the magnet was first placed and then was removed after 12 hours ("ON-OFF") or the magnet was not placed first but was placed after 12 hours ("OFF-ON"). As a result, at the left side (magnet side) of the substrate, stem cell adhesion was pronounced under the "ON" condition. Strikingly, when the magnet was placed after 12 hours, stem cell adhesion was dramatically improved at 48 hours ("OFF-ON") with significant increase in the adherent cell density by 66%, cell area by 51%, and focal adhesion number by 59%, which suggests that nano-ligands may be attracted to the magnet side at selected time points. Further, when the magnet was removed after 12 hours, stem cell adhesion remained similar without further increase at 48 hours ("ON-OFF"), which indicates that the nano-ligands, which were attracted to the magnet side, may have remained at the same side of the substrate.

Further, in the present invention, the spatiotemporally reversible tuning of nano-ligand sliding to regulate stem cell adhesion was investigated. As can be seen from c and d of FIG. 8, the position of the magnet was switched every 12 hours and higher cell adhesions were observed at the left, right, and left sides at 12 hours, 24 hours, and 36 hours, respectively.

FIG. 16 is a graph of a calculation of a density, an area, and an aspect ratio of adherent cells for spatiotemporally reversible conversion of the nano-ligand sliding according to the exemplary embodiment of the present invention. A density, an area, and an aspect ratio of adherent cells were calculated at the "left side" and "right side" of the substrate by using the time-lapse immunofluorescent confocal image for vinculin, F-actin, and nuclei after culturing the stem cells for 12 hours, 24 hours, and 36 hours at the "left side" and "right side" of the substrate illustrated in b of FIG. 11. The position of the permanent magnet was converted between two opposite sides for 12 hours each for three times under the "left" side of the substrate, then under the "right" side, and subsequently under the "left" side, and data is shown as mean±standard errors (n=30). Through this, it can be seen that the spatiotemporally reversible conversion of the nano-ligand sliding may control the adhesion of the stem cells.

Referring to b of FIG. 11 and FIG. 16, the spatiotemporally reversible conversion of the nano-ligand sliding controls the adhesion of the stem cells, and as illustrated in b of FIG. 11, the calculation of the density, area, and aspect ratio of the adherent cells in the "left" and "right" side of the substrate was made by using the time-lapse immunofluorescent confocal images for vinculin, F-actin, and nuclei after 12 hours, 24 hours, and 36 hours of culturing stem cells at the "left" and "right" side of the substrate. The position of the permanent magnet was converted between two opposite sides for 12 h each for three times under the "left" side of the substrate, then under the "right" side, and subsequently under the "left" side. Through this, the spatiotemporal reversibility of cell adhesion by sliding the slidable nano-ligand according to the present invention was proved, and the tissue-penetrative magnetic field-mediated spatiotemporal and reversible control of cellular adhesion presents the highly promising strategy for in vivo applications over the use of light.

Experimental Example 4

In order to confirm the change in mechanosensing-mediated stem cell differentiation through the in situ temporal control, the slidable nano-ligand according to the present invention was experimented as described below.

The integrin ligation-mediated adhesion and spreading of stem cells with mature FA formation activate mechanosensing signaling that can promote stem cell differentiation. Therefore, in the present invention, osteogenic differentiation of stem cells was investigated as a model of mechanosensing-mediated differentiation. The remote control of stem cell differentiation offers advantages in in vivo applications of tissue-regenerative therapies.

The mechanotransduction-mediated differentiation of stem cells was investigated by positioning a permanent magnet under the "left" side of the substrate under ROCK inhibition (with 50 μM of Y27632) or myosin II inhibition (with 10 μM of blebbistatin). The substrates with nanoparticles without RGD ligand or nano-ligand without application of a magnet were used to further confirm the effect of magnetically controlled nano-ligand sliding on the adhesion of stem cells. The differentiation of adherent stem cells under the nano-ligand sliding was investigated in osteogenic induction medium culture (basal growth medium supplemented with 10 mM β-glycerophosphate, 50 μM ascorbic acid-2-phosphate, and 100 nM dexamethasone).

Further, an alkaline phosphatase (ALP) staining-based analysis of the differentiation of stem cells under in situ control of the nano-ligand sliding was performed as described below. Stem cells after culture under the osteogenic differentiation medium were washed with PBS, treated with BCIP/NBT liquid (Sigma-Aldrich) for 30 minutes at a room temperature under dark conditions, and then washed with PBS. The treated stem cells were subsequently fixed with 4% (w/v) paraformaldehyde for 10 minutes and visualized using an optical microscope. The ALP-positive cells were counted out of the total number of cells from nuclei (DAPI)-staining.

FIG. 17 is an immunofluorescent confocal image of mechanosensing-mediated differentiation of the stem cells by in situ magnetic attraction of the slidable nano-ligands according to the exemplary embodiment of the present invention. a of FIG. 17 is an immunofluorescent image for RUNX2 and YAP with F-actin and nuclei and ALP expression in stem cells under a magnet. b of FIG. 17 is an immunofluorescent image for TAZ, integrin β1, FAK, and RhoA with F-actin and nuclei, YAP under ROCK inhibition (Y27632), and vinculin under myosin II inhibition (blebbistatin) in stem cells under a magnet. A scale bar indicates 50 μm. Referring to FIG. 17, it can be seen that the slidable nano-ligand promotes mechanosensing-mediated differentiation of stem cells through in situ magnetic attraction.

FIG. 18 is an immunofluorescent confocal image of stem cells in the absence of RGD ligand and permanent magnet of a Comparative Example. In particular, FIG. 18 is an immunofluorescent confocal image for RUNX2, F-actin, and nuclei as well as alkaline phosphatase (ALP) staining images after 7 days of culturing stem cells or immunofluorescent confocal image for YAP, F-actin, and nuclei after 2 days of culture. The adherent stem cells were imaged at the center of the left side of the substrate as indicated by red dotted rectangles in the schematic diagram. The "no RGD" and "no magnet" groups were used as controls. A scale bar indicates 50 μm. Referring to FIG. 18, it can be seen that in the "no RGD" or "no magnet" state, the differentiation of the stem cells by the nano-ligand sliding is not effectively controlled.

Referring to a of FIG. 17 and FIG. 18, significantly higher nuclear localization of RUNX2 in immunofluorescence and alkaline phosphatase-positive cells were observed on the left side (magnet side) of substrate. Concomitantly, nuclear localization of YAP that is a mechanosensitive transcription regulator was significantly enhanced on the left side. At the left side (magnet side) of the substrate, nuclear localization is consistent with temporal switching of stem cell adhesion in FIGS. 14 and 15.

FIG. 19 is a graph illustrating a result of an experiment of mechanotransduction and differentiation of stem cells for magnetic attraction of the slidable nano-ligand according to the exemplary embodiment of the present invention, in which a nuclear to cytoplasmic RUNX2 fluorescence ratio, alkaline phosphatase-positive cells, and a nuclear to cytoplasmic YAP fluorescence ratio are calculated after culturing stem cells. In particular, a nuclear to cytoplasmic RUNX2 fluorescence ratio, alkaline phosphatase-positive cells, and a nuclear to cytoplasmic YAP fluorescence ratio are calculated after culturing stem cells by positioning a permanent magnet under the "left side" of the substrate, and the calculation was made by using the immunofluorescent confocal images illustrated in a of FIG. 17 and FIG. 18. Data is shown as mean±standard errors (n=30). Statistically significant differences are indicated by different alphabets. Referring to FIG. 19, it can be seen that the magnetic attraction of the slidable nano-ligand promotes mechanotransduction and differentiation of the stem cells.

FIG. 20 is an immunofluorescent confocal image of an in situ time-regulated experiment of the nano-ligand sliding according to the exemplary embodiment of the present invention and a graph illustrating a calculation of a nuclear to a cytoplasmic RUNX2 fluorescence ratio. a of FIG. 20 is an immunofluorescent confocal image for RUNX2, F-actin, and nuclei after culturing stem cells for 7 days with a permanent magnet positioned under the left side of the substrate ("ON") or removed from the substrate ("OFF"). "ON" and "OFF" conditions were continuously applied for 7 days (RUNX2) of culture or switched after 12-hour culturing. Stem cells were imaged at the center of the "left" and "right" side of the substrate. A scale bar indicates 50 μm. b of FIG. 20 is a graph of a calculation of a nuclear to cytoplasmic RUNX2 fluorescence ratio. Data is shown as mean±standard errors (n=30). Statistically significant differences are indicated by different alphabets. Referring to FIG. 20, the slidable nano-ligand of the present invention may temporally control differentiation of stem cells by using the magnetic field.

FIG. 21 is a diagram illustrating a result of an experiment for mechanotransduction through time-regulated control of the slidable nano-ligand according to the exemplary embodiment of the present invention. a of FIG. 21 is an immunofluorescent confocal image for RUNX2, F-actin, and nuclei after culturing stem cells for 2 days with a permanent magnet positioned under the left side of the substrate ("ON") or removed from the substrate ("OFF"). b of FIG. 21 is a graph of a calculation of a nuclear to YAP fluorescence ratio. Referring to FIG. 21, the slidable nano-ligand of the present invention may control mechanotransduction of stem cells through the temporal control.

Referring to a and b of FIG. 20 and a and b of FIG. 21, differentiation and mechanotransduction of stem cells were both stimulated with more pronounced nuclear localization of RUNX2 and YAP under "ON" condition.

FIG. 22 is a diagram illustrating gene expression profiles of RUNX2 and ALP after culturing the stem cells for 7 days with the permanent magnet positioned under the "left side" of the substrate for the slidable nano-ligand according to the exemplary embodiment, and data is shown as mean±standard errors (n=30). Statistically significant differences are indicated by different alphabets.

Referring to FIG. 22, the gene expression analyses revealed significantly higher expression of RUNX2 and ALP on the left side (magnet side) under "ON" condition. Interestingly, on the left side (magnet side), both "OFF-ON" and "ON-OFF" conditions showed pronounced nuclear localization of RUNX2 and YAP that were comparable to "ON" condition. This indicates that magnet may be placed initially or subsequently to promote mechanotransduction and differentiation of stem cells because the nano-ligand may be attracted to the magnet side to activate the cellular signaling events at prescribed time points. Through this, it can be seen that differentiation of stem cells is stimulated through the in situ control of magnetically attracting the slidable nano-ligand.

Further, in the present invention, how integrin ligation-mediated activation of mechanotransduction signaling promotes stem cell differentiation under in situ nano-ligand sliding was investigated. In the present invention, a magnetic is positioned under the left side of the substrate, and diverse intracellular mechanosensitive pathways were investigated.

FIG. 23 is a diagram illustrating a result of a calculation of magnetic attraction of the slidable nano-ligand according to the exemplary embodiment of the present invention based on the immunofluorescent image. a of FIG. 23 is a result of quantification of the nuclear to cytoplasmic TAZ fluorescence ratio from the immunofluorescent confocal image for TAZ illustrated in b of FIG. 4. b of FIG. 23 is an immunofluorescent confocal image for p-FAK with F-actin and nuclei. c of FIG. 23 is a graph illustrating a nuclear to cytoplasmic YAP fluorescence ratio under ROCK inhibition (with Y27632) and d of FIG. 23 is a graph illustrating a cell area under myosin II inhibition (with blebbistatin) calculated from b of FIG. 17. The stem cells were cultured for 2 days with a permanent magnet positioned under the "left side" of the substrate. Adherent stem cells were imaged at the center of the "left" and "right" side of the substrate. A scale bar indicates 50 μm. Data is shown as mean±standard errors (n=30). Statistically significant differences are indicated by different alphabets. Referring to FIG. 23, it can be seen that the slidable nano-ligand of the present invention facilitates focal adhesion and mechanosensing of the stem cells through the control of magnetic attraction.

Referring to b of FIG. 17 and a to d of FIG. 23, higher nuclear localization of TAZ, a transcription co-activator, and integrin β1 activation in immunofluorescence were observed at the left side (magnet side) of the substrate. Stable formation of FA complexes includes focal adhesion kinase (FAK), which phosphorylates to activate mechanosensitive RhoA. On the left side (magnet side), FAK was highly expressed, which was phosphorylated and activated to stimulate pFAK. The focal adhesion-mediated activation of mechanotransduction stimulated RhoA at the left side, which activated rho-associated protein kinase (ROCK) to induce nuclear localization of YAP, as revealed by ROCK inhibition with Y27632. Furthermore, myosin II inhibition with blebbistatin significantly reduced cell spread area at the left side. Through the result, it can be seen that in situ control of attracting slidable nano-ligand facilitates integrin ligation to form an FA assembly that activates mechanosensing-mediated differentiation of stem cells.

Experimental Example 5

In order to confirm that the slidable nano-ligand according to the present invention spatially controls the adhesion of stem cells in vivo through the in situ control, a following experiment was carried out.

The in situ remote control of nano-ligand sliding by using the slidable nano-ligand according to the present invention is applicable in vivo. Recently, UV light was utilized for spatial modulation of cell adhesion in vivo. However, in this study, UV light was found to be highly absorbed by living tissues in vivo, which may induce severe cytotoxicity. In contrast, an external magnetic field-based control of spatial regulation of cell adhesion in vivo presents a promising tissue-penetrative and cytocompatible control strategy.

In order to investigate the effect of the in situ control of nano-ligand sliding for the adhesion of stem cells in vivo, the substrate including the slidable nano-ligand was subcutaneously implanted into 14 2-month old nude mice. Prior to the implantation, the nude mice were subjected to an intraperitoneal injection of a mixture of 5 μL of zoletil, 2 μL of rompun, and 3 μL of saline. 2 cm-long incision was made on the back of the mice. Following the implantation, hMSCs were injected onto the substrate at 100 k/mL and a permanent magnet was attached under the left side (abdomen side) of the substrate to promote sliding of nano-ligands toward the left side. The anesthesia was maintained until the collection of the substrate for confocal imaging of immunofluorescence.

FIG. 24 is a diagram illustrating a result of an experiment of magnetic control of attracting the slidable nano-ligand according to the exemplary embodiment of the present invention. a of FIG. 24 is an image illustrating an experiment of a magnetic control of nano-ligands, and b of FIG. 24 is a diagram illustrating a result of immunofluorescence for human-specific HuNu with actin and nuclei of stem cells injected onto a slidable nano-ligand-presenting substrate after subcutaneous implantation with a magnet ("ON") or without a magnet ("OFF"). c of FIG. 24 is a graph illustrating quantification of in vivo adhered cell density and area. A scale bar indicates 50 μm. Referring to FIG. 24, it can be seen that the slidable nano-ligand facilitates the adhesion of stem cells in vivo through the magnetic control.

In the present invention, as illustrated in a of FIG. 24, the substrate representing the slidable nano-ligand was subcutaneously implanted into the backs of the nude mice to which hMSC was injected. Next, the magnet was placed under the left side (abdomen of mice) of the substrate ("ON") and was not placed as control experiments ("OFF"). As a result, referring to b and c of FIG. 24, the immunofluorescent confocal images for human-specific nuclear antigen (HuNu) with actin and nuclei revealed that all adherent cells were hMSCs, which adhered to the left side (magnet side) of the substrate in significantly higher density by 75% and spread cell area by 44% than the right side under the "ON" condition. In stark contrast, stem cells adhered to the left and right side in compatible cell density and area under "OFF" condition. Through the result, the in situ remote control of nano-ligand sliding may be translated into a complex in vivo environment to spatially control stem cell adhesion. Further, it was confirmed that the in situ remote control is effective in spatial regulation of diverse host cells in vivo.

Accordingly, the magnetic field-based spatiotemporal control of the slidable nano-ligand according to the present invention may effectively control stem cell adhesion both ex vivo or in vivo, and resultant mechanotransduction-regulated differentiation.

In the Experimental Example, an immunofluorescent staining-based analysis of the adhesion and differentiation of stem cells under the in situ control of nano-ligand sliding was carried as described below. Stem cells after culture were fixed with 4% (w/v) paraformaldehyde at a room temperature for 10 minutes and washed with PBS. The fixed cells were blocked with 3% (w/v) BSA and 0.1% (v/v) Triton-X (Sigma Aldrich) in PBS at the room temperature for 30 minutes. The blocked cells were treated with primary antibody (integrin β1, vinculin, RUNX2, YAP, TAZ, p-FAK, FAK, RhoA, and HuNu) at 4° C. for 16 hours and washed with PBS. The cells were treated with secondary antibody, phalloidin, and DAPI at the room temperature for 30 minutes and washed with PBS. The immunofluorescently stained cells were imaged under a confocal microscope (LSM700, Carl Zeiss) under identical exposure conditions for all the compared groups and then analyzed by ImageJ software as previously shown.

Further, in order to quantitate the adhesion, differentiation, and mechanosensing of stem cells under nano-ligand sliding, immunofluorescently stained images were subjected to the analyses by Image J software. For integrin β1, staining intensities were calculated from five different images by a histogram function. For the adherent cell density, the number of cellular nuclei was calculated from 5 different DAPI-stained images. For adherent cell area and aspect ratio (major axis/minor axis), five different phalloidin-stained images were used for the calculation. For the number of focal adhesion, five different vinculin-stained images were used for counting clusters with the size greater than 1 $\mu m^2$ as previously reported. For differentiation (RUNX2) and mechanotransduction (YAP) of stem cells, a fluorescence ratio of nucleus to cytoplasm of stem cells from five different images was used for calculations.

Further, a quantitative reverse transcription-polymerase chain reaction (qRT-PCR)-based analysis of the differentiation of stem cells under in situ control of nano-ligand sliding was carried out as described below. Stem cells after culture under osteogenic differentiation medium were collected by Trizol (1 mL per group) applied onto the substrate (with separated left and right side) to extract RNA. For each group, 1 μg of RNA was used for reverse transcription to cDNA by using a High-Capacity RNA-to-cDNA kit. The StepOne Plus Real-Time PCR System (Applied Biosystems) was used for real-time PCR reactions with Sybr Green assays. The expression of target gene (RUNX2 and ALP) was normalized with that of GAPDH and then presented as fold expression.

controlling adhesion and differentiation of stem cells by treating the nano-ligand presenting substrate with stem cells and then applying an external magnetic field, wherein the manufacturing of the nano-ligand presenting substrate includes:

soaking the surface of the substrate in an acid solution;

activating the surface of the substrate by putting the soaking-completed substrate in an amino-silane solution; and treating the activated substrate by using ultrasonic waves at a room temperature.

2. The method of claim 1, wherein the controlling the adhesion and differentiation of the stem cells is performed by positioning the nano-ligand presenting substrate in vivo or ex vivo and then applying a magnetic field of 100 to 700 mT for 12 to 48 hours.

3. The method of claim 1, wherein the controlling the adhesion and differentiation of the stem cells is performed by changing a location of a magnetic field applied to the substrate.

4. The method of claim 1, wherein the controlling the adhesion and differentiation of the stem cells is performed by changing a location of a magnetic field applied to the substrate over time.

5. A method of promoting cell adhesion and differentiation of stem cells, the method comprising:

manufacturing a nano-ligand presenting substrate by putting a substrate, of which a surface is activated, in a solution including a nano-ligand for promoting adhe-

What is claimed is:

1. A method of promoting cell adhesion and differentiation of stem cells, the method comprising:

manufacturing a nano-ligand presenting substrate by putting a substrate, of which a surface is activated, in a solution including a nano-ligand for promoting adhesion and differentiation of stem cells, the nano-ligand comprising a core including magnetic nano-particles, a coating layer provided to surround the core and including an integrin-binding ligand peptide, and a linker provided between the core and the coating layer, wherein the integrin-binding ligand peptide is negatively charged; and sion and differentiation of stem cells, the nano-ligand comprising a core including magnetic nano-particles, a coating layer provided to surround the core and including an integrin-binding ligand peptide, and a linker provided between the core and the coating layer, wherein the integrin-binding ligand peptide is negatively charged; and controlling adhesion and differentiation of stem cells by treating the nano-ligand presenting substrate with stem cells and then applying an external magnetic field, wherein the substrate, of which the surface is activated, is obtained by putting the substrate in an amino-silane solution.

* * * * *

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: synthetic sequence

<400> SEQUENCE: 1

Cys Asp Asp Arg Gly Asp
1               5
```